(12) United States Patent
Lambert

(10) Patent No.: US 12,042,625 B2
(45) Date of Patent: Jul. 23, 2024

(54) DEVICES AND METHODS FOR PROTECTING A USER FROM A SHARP TIP OF A MEDICAL NEEDLE

(71) Applicant: EMED Technologies Corporation, El Dorado Hills, CA (US)

(72) Inventor: Paul Lambert, El Dorado Hills, CA (US)

(73) Assignee: EMED Technologies Corporation, El Dorado Hills, CA (US)

( * ) Notice: Subject to any disclaimer, the term of this patent is extended or adjusted under 35 U.S.C. 154(b) by 1025 days.

(21) Appl. No.: 16/455,299

(22) Filed: Jun. 27, 2019

(65) Prior Publication Data
US 2019/0321549 A1 Oct. 24, 2019

Related U.S. Application Data

(60) Continuation of application No. 15/090,040, filed on Apr. 4, 2016, now Pat. No. 10,350,350, which is a
(Continued)

(51) Int. Cl.
*A61M 5/158* (2006.01)
*A61M 5/162* (2006.01)
(Continued)

(52) U.S. Cl.
CPC ............ *A61M 5/158* (2013.01); *A61M 5/162* (2013.01); *A61M 5/1626* (2013.01); *A61M 5/32* (2013.01); *A61M 5/321* (2013.01); *A61M 5/3243* (2013.01); *A61M 5/3257* (2013.01); *A61M 25/0618* (2013.01); *A61M 25/0637* (2013.01);
(Continued)

(58) Field of Classification Search
CPC .... A61M 5/158; A61M 5/162; A61M 5/1626; A61M 5/32; A61M 5/321; A61M 5/3243; A61M 5/3257; A61M 25/0618; A61M 25/0637; A61M 5/3275; A61M 2005/1581; A61M 2005/325; A61M 2005/3256; A61M 5/14; A61M 5/3202; A61M 5/3205; A61M 5/3216; A61M 5/3245; A61M 2005/3246; A61M 2005/3258; A61M 25/0612; A61M 25/0625; A61M 25/0631; A61B 50/3001; A61B 50/362
See application file for complete search history.

(56) References Cited

U.S. PATENT DOCUMENTS

| | | | | |
|---|---|---|---|---|
| 5,147,319 A | * | 9/1992 | Ishikawa | A61M 25/0637 604/174 |
| 2002/0111581 A1 | * | 8/2002 | Sasso | A61M 5/158 604/93.01 |
| 2006/0167420 A1 | * | 7/2006 | Saldell | A61M 5/3216 604/192 |

* cited by examiner

*Primary Examiner* — Jason E Flick
(74) *Attorney, Agent, or Firm* — Jones Day

(57) ABSTRACT

A device for protecting a user from a sharp tip of a medical needle includes a central body portion, a medical needle having a sharp tip, a pair of wings in attachment to the central body portion, and a hook-and-loop fastening system disposed on at least one of the wings, and configured to selectively attach the wings together with the medical needle positioned between the wings so as to protect a user from the sharp tip of the medical needle. A method of using the device includes withdrawing a sharp tip of a medical needle from a patient, closing a pair of wings with the medical needle positioned between the wings, and fastening the wings together with the medical needle positioned between the wings so as to protect a user from the sharp tip of the medical needle.

20 Claims, 35 Drawing Sheets

Related U.S. Application Data division of application No. 13/931,226, filed on Jun. 28, 2013, now Pat. No. 9,308,322, which is a continuation-in-part of application No. 12/187,256, filed on Aug. 6, 2008, now Pat. No. 8,500,703.

(60) Provisional application No. 61/130,880, filed on Jun. 2, 2008.

(51) Int. Cl.
*A61M 5/32* (2006.01)
*A61M 25/06* (2006.01)

(52) U.S. Cl.
CPC ... *A61M 2005/1581* (2013.01); *A61M 5/3216* (2013.01); *A61M 2005/3217* (2013.01); *A61M 2005/325* (2013.01); *A61M 2005/3256* (2013.01); *A61M 5/3275* (2013.01)

DEVICES AND METHODS FOR PROTECTING A USER FROM A SHARP TIP OF A MEDICAL NEEDLE

RELATED APPLICATIONS

The present patent document is a continuation of U.S. patent application Ser. No. 15/090,040, filed on Apr. 4, 2016, which is a divisional of U.S. patent application Ser. No. 13/931,226, filed on Jun. 28, 2013 and that issued as U.S. Pat. No. 9,308,322 on Apr. 12, 2016, which in turn is a continuation-in-part of U.S. patent application Ser. No. 12/187,256, filed on Aug. 6, 2008 and that issued as U.S. Pat. No. 8,500,703 on Aug. 6, 2013, which claimed priority from U.S. Provisional Pat. App. Ser. No. 61/130,880, filed on Jun. 2, 2008, each of which are hereby incorporated by reference.

TECHNICAL FIELD

The present invention relates to a device, system and method for protecting a user from a sharp tip of a medical needle.

BACKGROUND

Generally, Huber needles, subcutaneous needles, and other types of medical needles with sharp tips are inserted by medical workers for medical procedures into patients. These users typically have to carefully maintain the sharp tip during and after removal of the medical needle from the patient until the medical needle is properly disposed of in a biohazard container. As this sharp tip is contaminated with blood or other fluids from the patient, it is considered a significant hazard.

Due to difficulties with the patient, including both physical and mental issues, the carrier portion with the medical needle often is not handled with the degree of care necessary by the user. In contending with various patient issues, a user may become injured by the sharp tip of the needle. FIG. 1 illustrates an example of a device 100 having a sharp tip 102 at the end of a medical needle 104 between a pair of wings 106, 108. Wings 106, 108 are positioned to allow placement of needle 104 into a patient, and to assist with removal of needle 104 from the patient. However, wings 106, 108 provide little, if any, protection to a user from needle 104 during or after removal from the patient.

Various safety devices have been used as an attempt to ameliorate the danger of the medical needle. However, the currently known safety devices are generally not designed to meet clinical protocols and are difficult to use with other devices. Current devices tend to have a profile which will extend away from a patient's body.

BRIEF SUMMARY

In an embodiment, there is provided a device for protecting a user from a sharp tip of a medical needle, the device comprising a central body portion in fluid connection with a delivery tube; a medical needle having a first end and a second end in opposition to one another, the first end in fluid connection with the central body portion and the delivery tube, and the second end of the needle extending away from the central body portion to a sharp tip, and a line from the first end to the second end of the medical needle defining a longitudinal axis; a pair of wings having an inner region and an outer region, the inner region of each one of the pair of wings in attachment to the central body portion, the outer region of each one of the pair of wings extending away from the central body portion, the pair of wings disposed in opposition to one another with the medical needle positioned therebetween, and the pair of wings being selectively positionable from a first position to a second position, the first position for placing the medical needle into a patient and delivering a medicinal fluid to a second position, and the second position for removing the medical from the patient; and a mechanical fastener disposed on at least one of the pair of wings, the mechanical fastener configured to selectively attach the pair of wings together with the medical needle positioned therebetween so as to protect a user from the sharp tip of the medical needle.

In another embodiment, there is provided a device for protecting a user from a sharp tip of a medical needle, the device comprising a central body portion in fluid connection with a delivery tube; a medical needle having a first end and a second end in opposition to one another, the first end in fluid connection with the central body portion and the delivery tube, and the second end of the needle extending away from the central body portion to a sharp tip, and a line from the first end to the second end of the medical needle defining a longitudinal axis; and a sleeve slidably disposed in a surrounding configuration to the central body portion, a sliding mechanism formed by the sleeve and the central body portion allowing movement of the sleeve from a first position to a second position, the sleeve in the first position providing the medical needle in a configuration for insertion into a patient and delivery of a medicinal fluid in the patient, and the sleeve in the second position covering the medical needle so as to protect a user from the sharp tip of the medical needle.

In yet another embodiment, there is provided device for protecting a user from a sharp tip of a medical needle, the device comprising a central body portion in fluid connection with a delivery tube; a medical needle having a first end and a second end in opposition to one another, the first end in fluid connection with the central body portion and the delivery tube, and the second end of the needle extending away from the central body portion to a sharp tip, and a line from the first end to the second end of the medical needle defining a longitudinal axis; and a frame member having a polygonal structure extending from the central body portion, the polygonal structure having a first hinged portion, a second hinged portion, a third hinged portion, and a fourth hinged portion, the first hinged portion positioned at the central body portion, the second hinged portion positioned in opposition to the first hinged portion, the third hinged portion and the fourth hinged portion positioned, in opposition to one another, between the first hinged portion and the second hinged portion, the polygonal structure forming an opening at the second hinged portion sized for passage of the medical needle, the polygonal structure selectively positionable from a first position to a second position, the first position configured with the first hinged portion and the second hinged portion in an open configuration, and the third hinged portion and the fourth hinged portion in a closed configuration, with the medical needle extended through the opening for placement into a patient and delivery of a medicinal fluid, and the second position configured with the first hinged portion and the second hinged portion in a closed configuration, and the third hinged portion and the fourth hinged portion in an open configuration, with the polygonal structure surrounding the medical needle so as to protect a user from the sharp tip of the medical needle.

In still another embodiment, there is provided a method of protecting a user from a sharp tip of a medical needle, the method comprising withdrawing a sharp tip of a medical needle from a patient; closing a pair of wings with the medical needle positioned therebetween; and fastening the pair of wings together with the medical needle positioned therebetween so as to protect a user from the sharp tip of the medical needle.

In another embodiment, there is provided a method of protecting a user from a sharp tip of a medical needle, the method comprising withdrawing a sharp tip of a medical needle from a patient; and sliding a sleeve slidably disposed in a surrounding configuration to a central body portion from a first position providing the medical needle in a configuration for insertion into the patient and delivery of a medicinal fluid in the patient to a second position covering the medical needle so as to protect a user from the sharp tip of the medical needle.

In yet another embodiment, there is provided a method of protecting a user from a sharp tip of a medical needle, the method comprising withdrawing a sharp tip of a medical needle from a patient through an opening formed in a polygonal structure of frame member; and articulating hinges of the polygonal structure to close the frame member surrounding the medical needle so as to protect a user from the sharp tip of the medical needle.

It is to be understood that the scope of the invention is to be determined by the scope of the claims as issued. Nothing in this Summary or the Background is to be construed as requiring a feature set forth herein or that a given embodiment address issues identified in the Background. In this regard, there are other aspects and features of varying embodiments. This will become apparent as the Specification proceeds.

The construction of the invention, however, together with additional objects and advantages thereof will be best understood from the following description of the specific embodiment when read in connection with the accompanying drawings.

BRIEF DESCRIPTION OF THE DRAWINGS

For a fuller understanding of the nature of the present invention, reference should be made to the following detailed description, taken in connection with the accompanying drawings in which like reference numerals refer to like elements and in which.

DETAILED DESCRIPTION

Referring to FIGS. 2-15, there are provided devices for protecting a user from a sharp tip of a medical needle. These safety devices provide protection to eliminate needle stick injuries when using needles associated with subcutaneous fluid administration as well as access to implanted ports.

Subcutaneous sets needles and sets are used to infuse a pharmaceutical product into the subcutaneous tissue. During the insertion and removal, the needle is exposed to users and may cause needle-stick injuries. In addition to subcutaneous needle, Huber needle sets (otherwise known as non-coring needles) are used to infuse a pharmaceutical product into a previously implanted port (which is typically made from titanium). The port has a septum space defined between the titanium port body and an elastic membrane that covers it. Huber needles are inserted through the skin into the port.

Conventional Huber devices can pose difficulty when removing from the patient. A clinician may need to apply a significant amount of force to remove the device. During this process, the needle may free suddenly, as a result of the force applied, and increase the risk of accidental needle stick injury from the exposed needle.

The safety devices described herein include, but are not limited to, subcutaneous needles and Huber needles. The safety devices improve user safety during removal of the needle from the patient. The safety devices described herein may also be applied to other devices that have needles.

Figure 1:
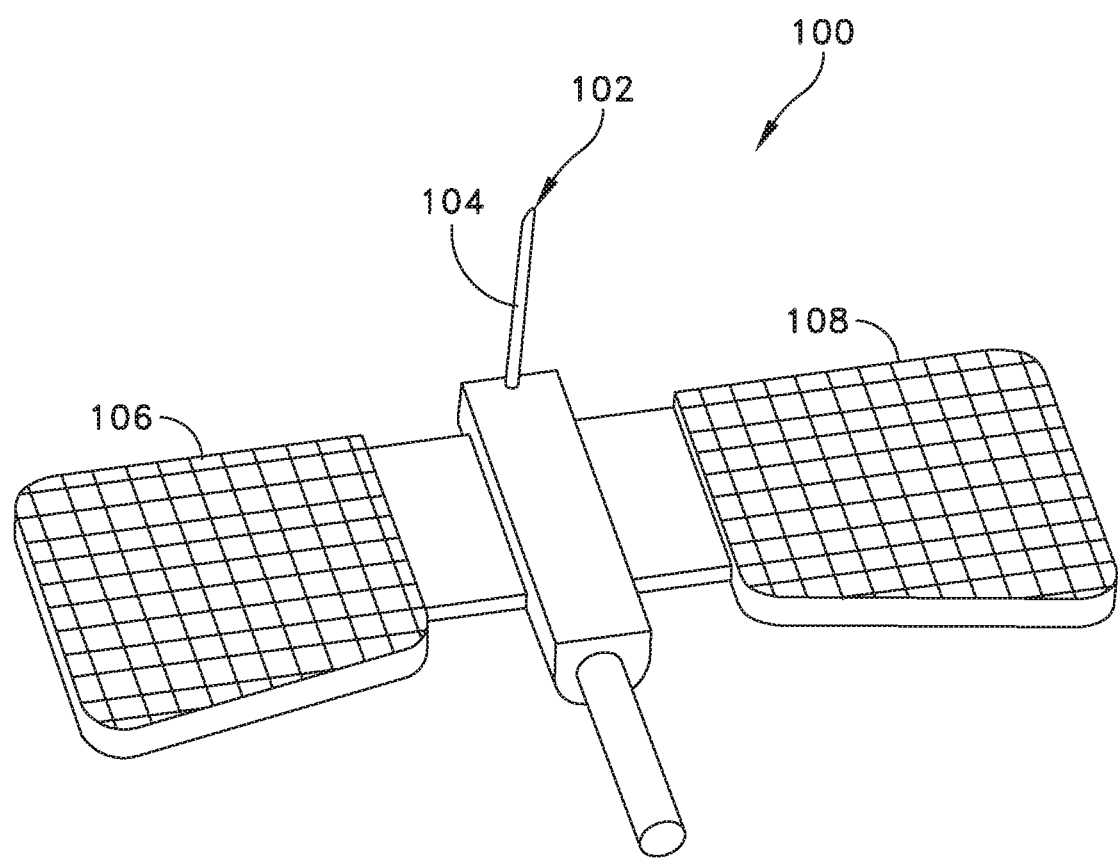
FIG. 1 illustrates a prior art device having a needle associated with subcutaneous fluid administration.
Figure 2:
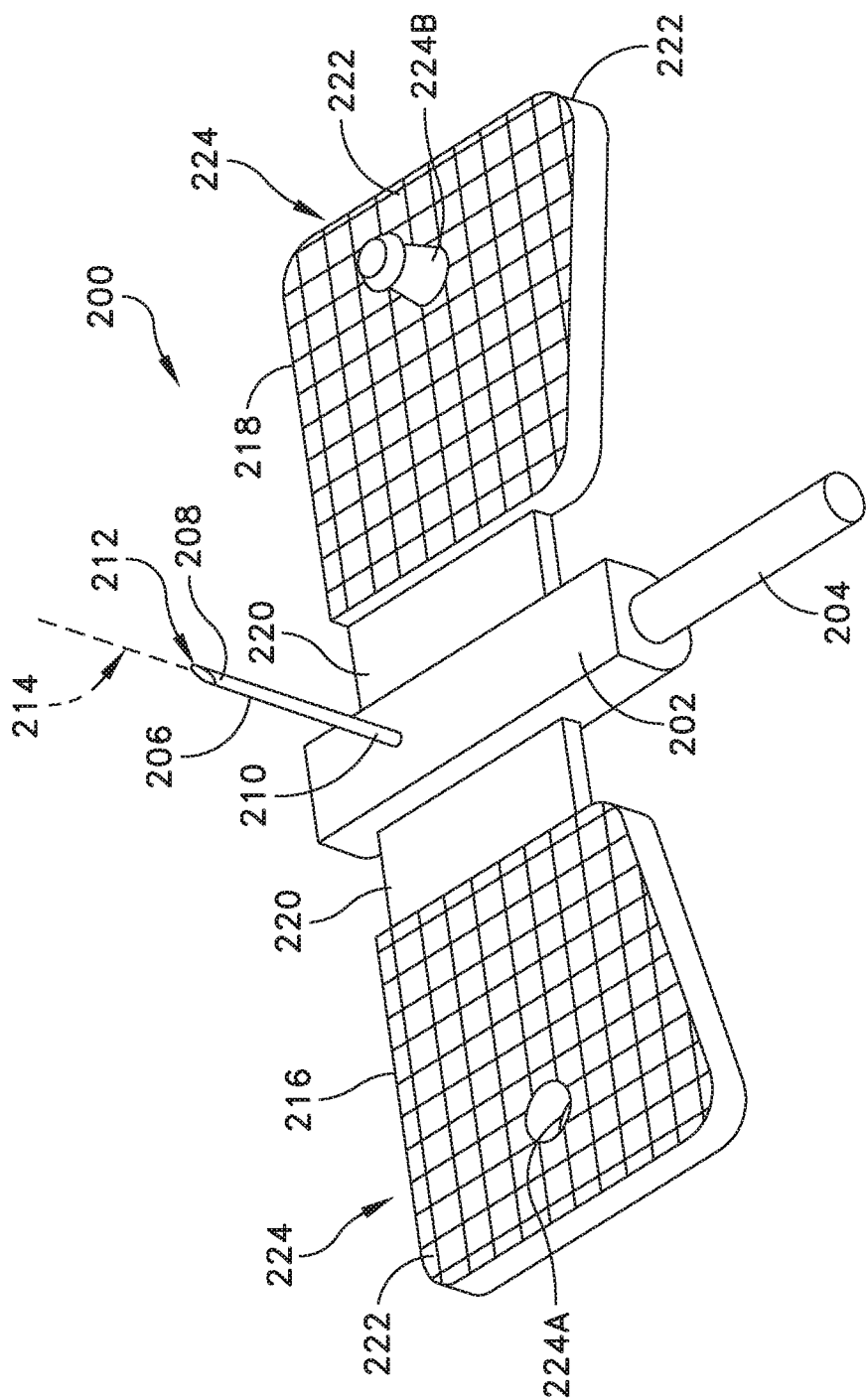
FIG. 2 illustrates an exemplary safety device with a mechanical fastener of an orifice and a pin in wing portions.
Figure 3:
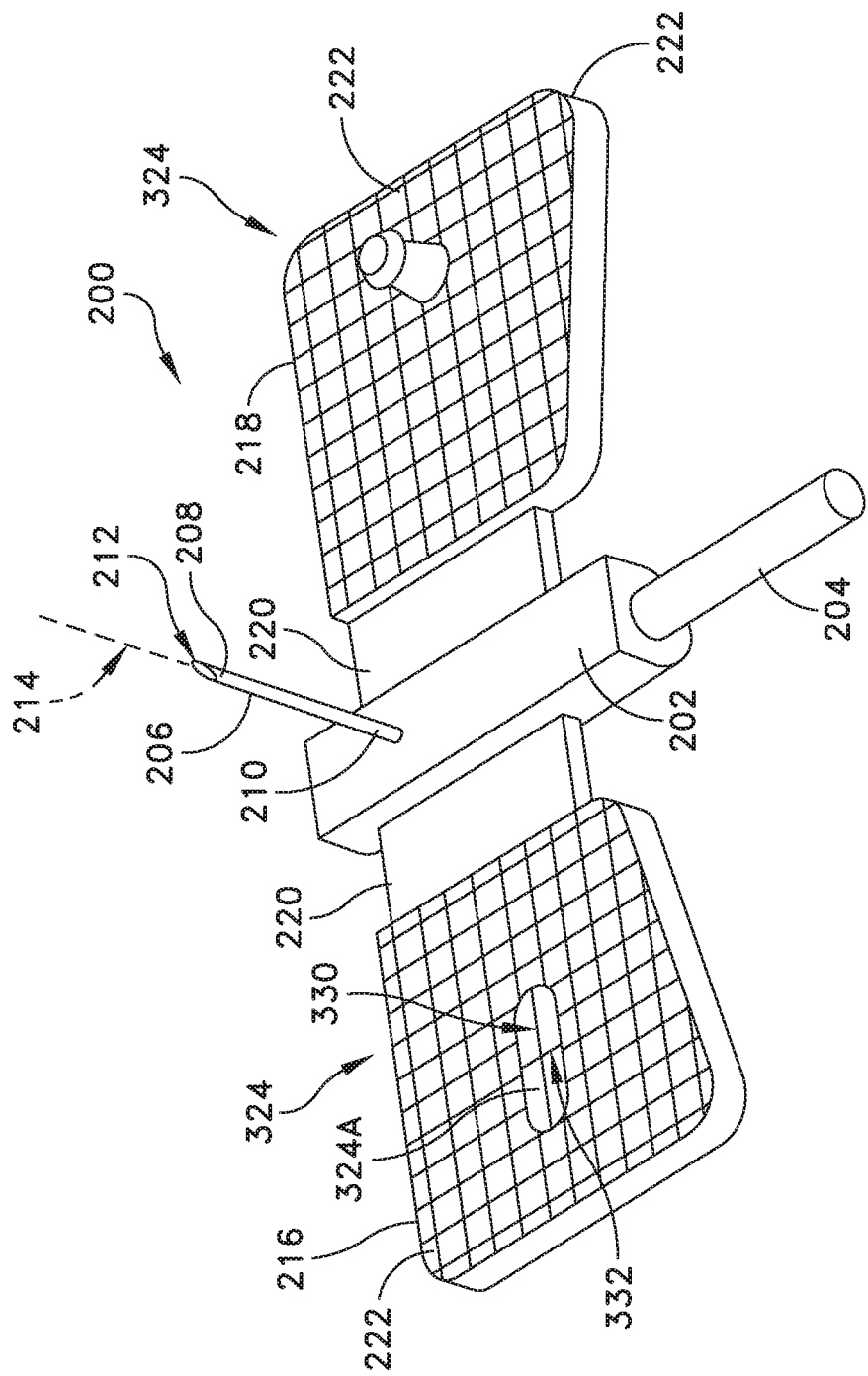
FIG. 3 illustrates another safety device with a mechanical fastener of an elongated orifice and a pin in the wing portions.
Figure 4:
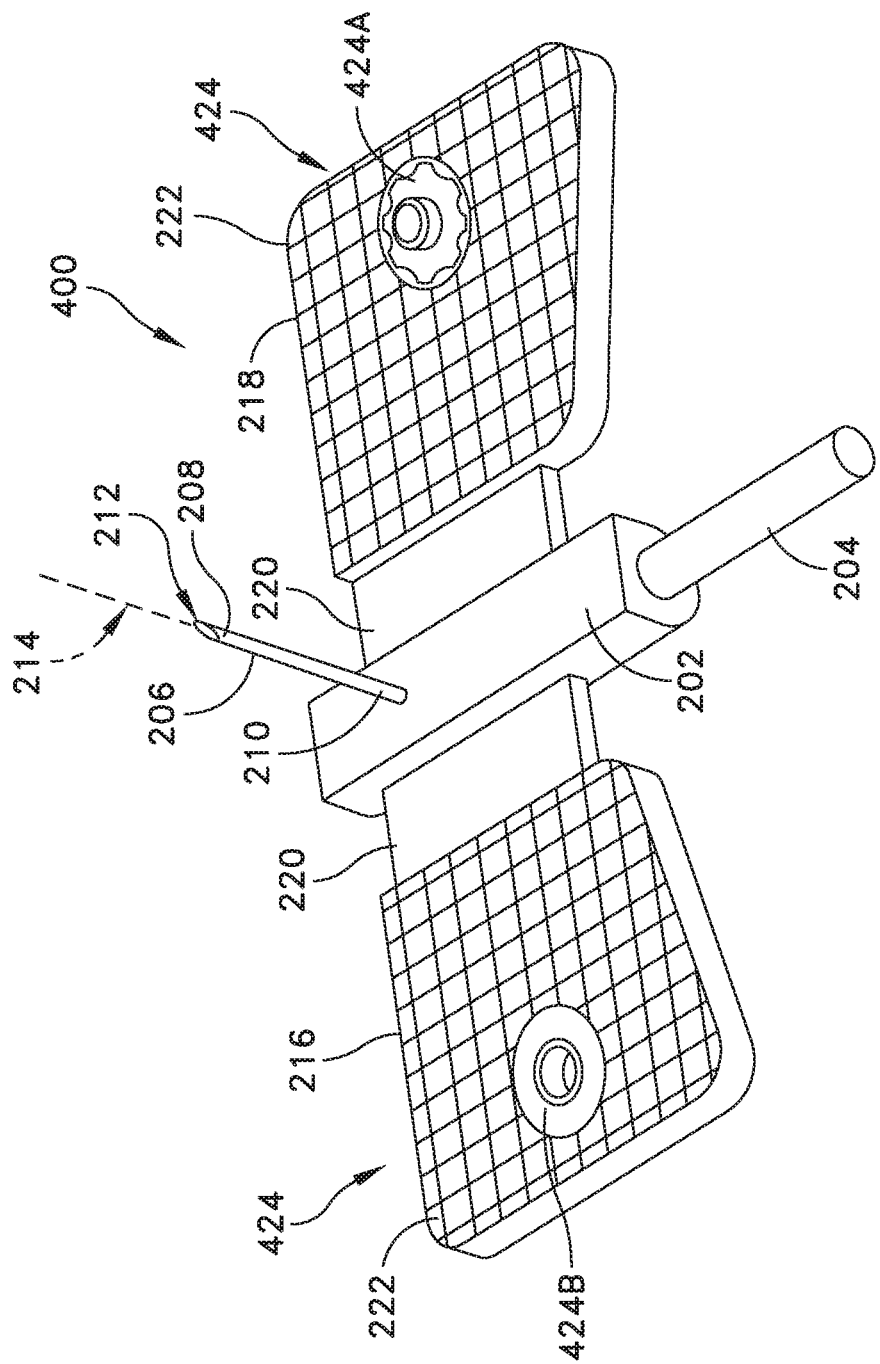
FIG. 4 illustrates a safety device with a mechanical fastener of a snap button in the wing portions.

A device 200, which is shown in FIG. 2, may include a central body portion 202 in fluid connection with a delivery tube 204. A medical needle 206 has a first end 208 and a second end 210 in opposition to one another. First end 208 is in fluid connection with central body portion 202 and delivery tube 204. Second end 210 of needle 206 may extend away from central body portion 202 to a sharp tip 212. A line from first end 208 to second end 210 of medical needle defines a longitudinal axis 214.

A pair of wings 216, 218 have an inner region 220 and an outer region 222. Inner region 220 of each one of the pair of wings 216, 218 may be provided in attachment to central body portion 202. Outer region 222 of each one of the pair of wings 216, 218 may extend away from central body portion 202. The pair of wings 216, 218 disposed in opposition to one another with the medical needle positioned therebetween, and the pair of wings 216, 218 being selectively positionable from a first position to a second position. The first position may be generally configured for placing medical needle 206 into a patient and delivering a medicinal fluid. The second position may be configured for removing the medical needle 206 from the patient.

A mechanical fastener 224 may be disposed on at least one of pair of wings 216, 218. Mechanical fastener 224 may be configured to selectively attach the pair of wings 216, 218 together with medical needle 206 positioned in between wings 216, 216. This attachment of the wings 216, 218 protects a user from sharp tip 212 of medical needle 206. In one embodiment, fastener 224 may include portions 224A and 224B.

Figure 11:
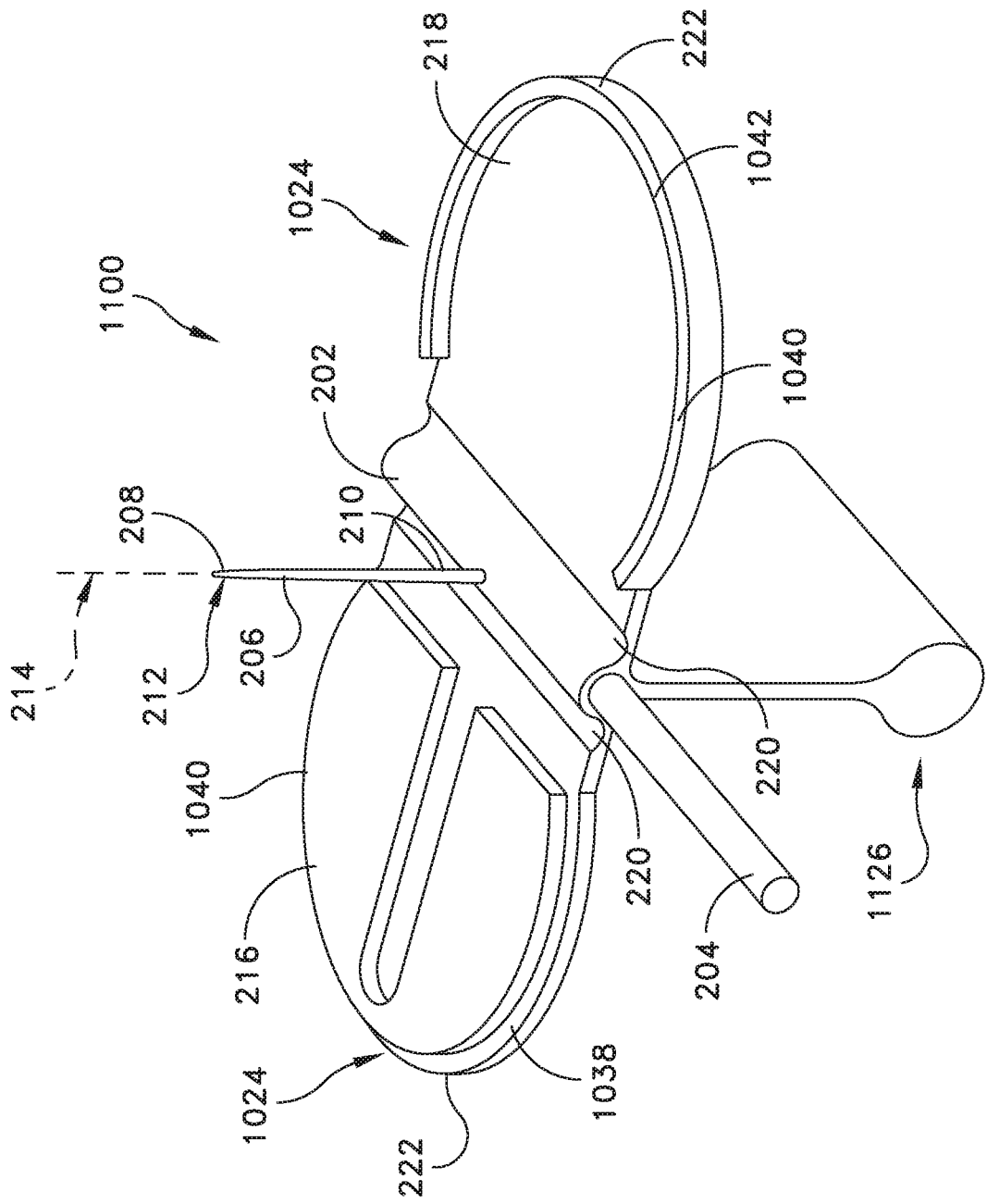
FIG. 11 illustrates a safety device, similar to the one of FIG. 10, which further includes a handle.

Optionally, central body portion 202 may include a handle. For example, FIG. 11 illustrates a handle 1126 extending from central body portion 202.

Referring to FIG. 2, mechanical fastener 224 may include one of wings 216, 218 with an orifice 224A and a pin 224B extending from other one of wings 216, 218. Orifice 224A and pin 224B may be configured to engage with one another to selectively attach the pair of wings 216, 218 together with medical needle 218 positioned between wings 216, 216. This attachment of the wings 216, 218 protects a user from sharp tip 212 of medical needle 206.

Orifice 224A has a diameter 226. Pin 224B also has a diameter 228. In one embodiment, diameter 226 of orifice 224A is shorter than the diameter 228 of pin 224B. Looking at FIG. 3, there is shown a device 300 having mechanical fastener 324. In one embodiment, mechanical fastener may include portions 324A and 324B. For example, an orifice 324A is provided with a major axis 330 and a minor axis 332. A pin 324B is provided with a diameter 328. Major axis 330 of orifice 324A is longer than diameter 328 of pin 324B. Minor axis 324B of orifice 324B is shorter than diameter 328 of pin 324B.

In an embodiment, a device 400 (FIG. 4) with mechanical fastener 424 may include a male portion 424A and a female portion 424B. For example, mechanical fastener may be configured as a snap button 424 Male portion 424A of snap button 424 may be mounted to one of wings 216, 218. Female portion 424B of snap button 424B may be mounted to the other one of the wings 216, 218. Male portion 424A and female portion 424B of snap button 424 are configured to engage with one another to selectively attach the pair of wings 216, 218 together with the medical needle 206 positioned between wings 216, 218. This attachment of the wings 216, 218 protects a user from sharp tip 212 of medical needle 206.

Figure 5:
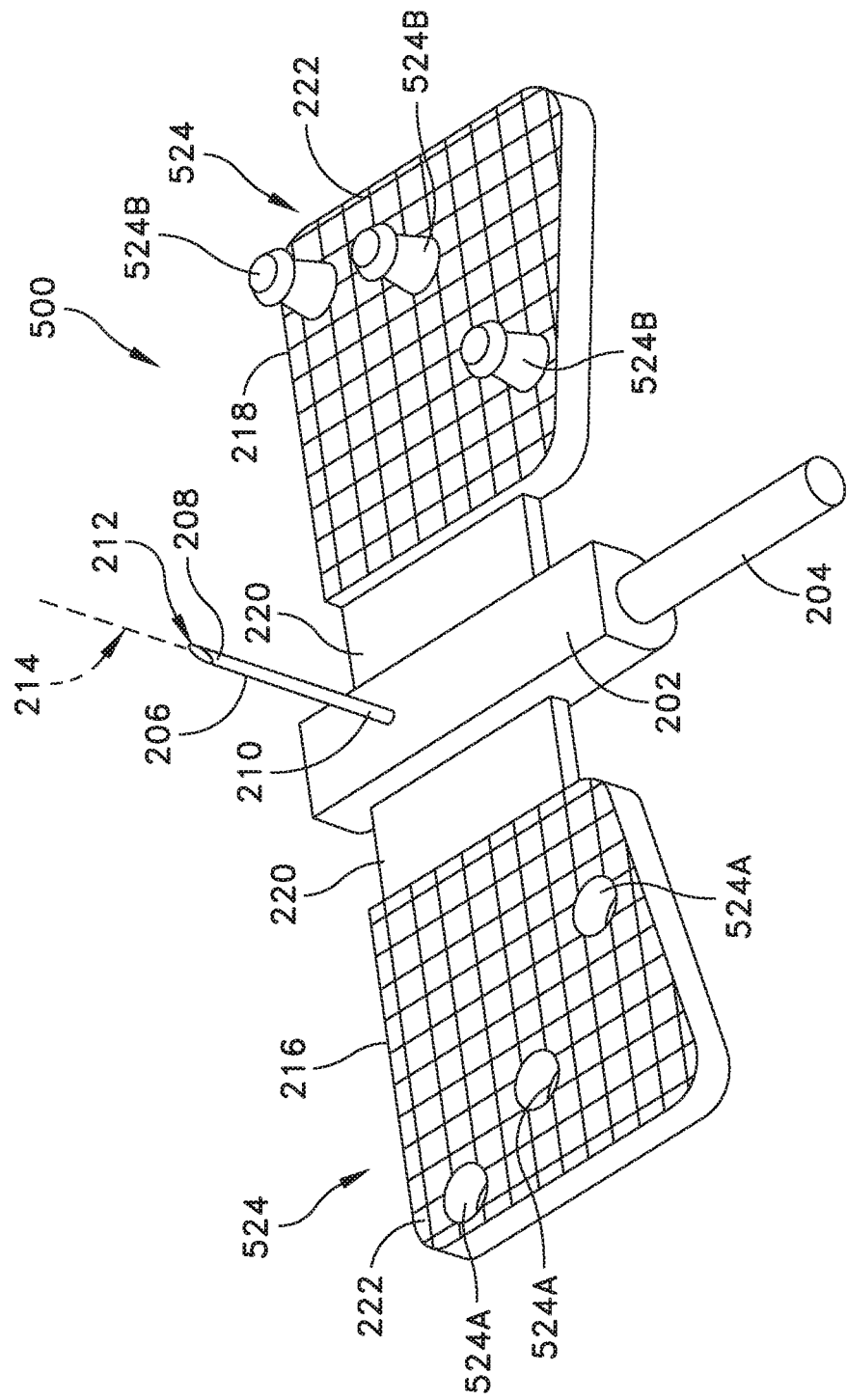
FIG. 5 illustrates a safety device with a mechanical fastener of a plurality of elongated orifices and a plurality of pins in the wing portions.

Referring now to FIG. 5, and in an embodiment, a device 500 may include mechanical fastener 524 with female portions 524A and a male portions 524B. For example, one of the wings 216, 218 forms a plurality of orifices 524A and the other one of the wings 216, 218 has a plurality of pins 524B. The plurality of pins 524B and the plurality of orifices 524A may be configured to engage with one another to selectively attach the pair of wings 216, 218 together with medical needle 206 positioned between wings 216, 218. This attachment of the wings 216, 218 protects a user from sharp tip 212 of medical needle 206.

Figure 6:
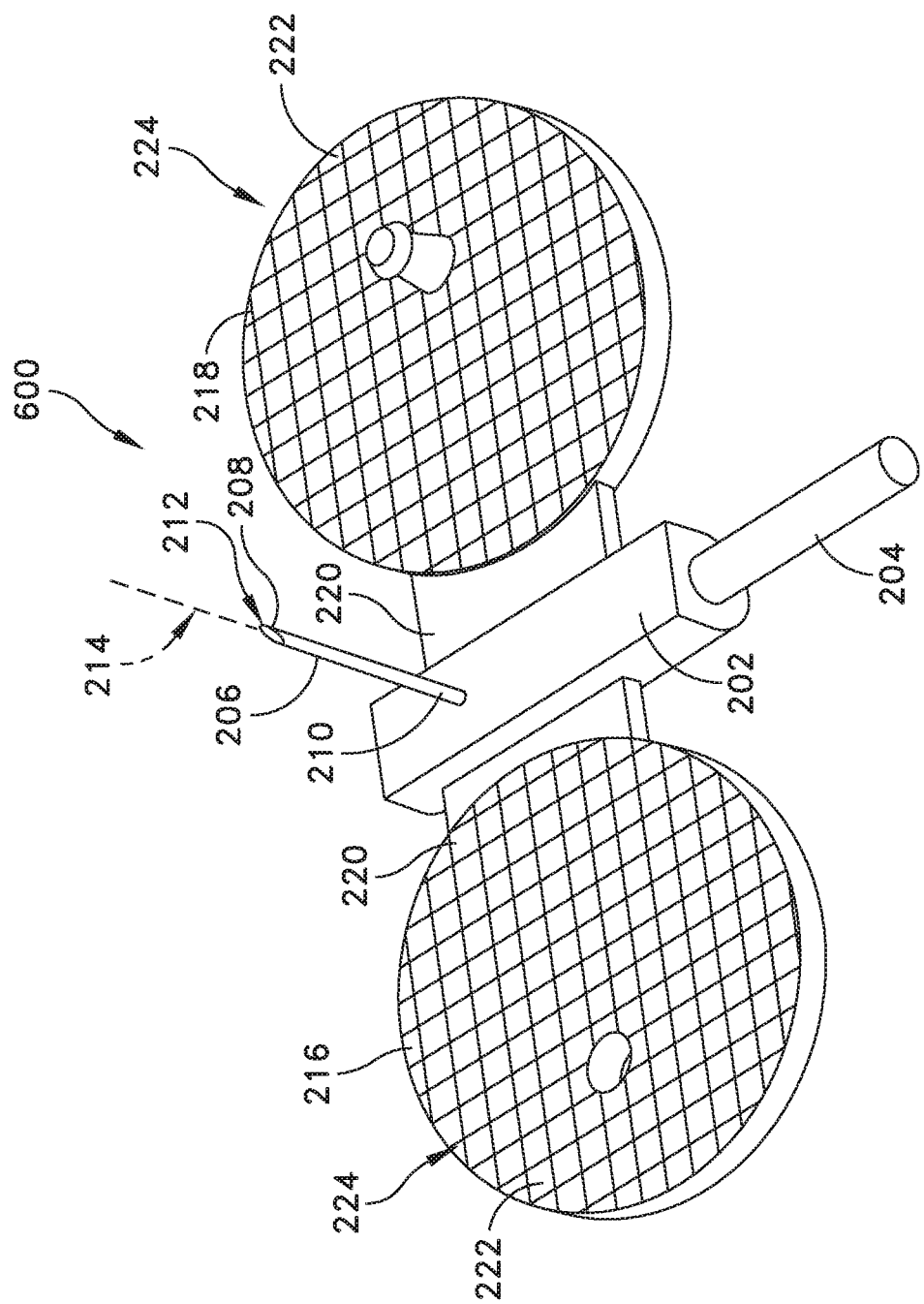
FIG. 6 illustrates a safety device with a mechanical fastener having a circular shape.
Figure 7:
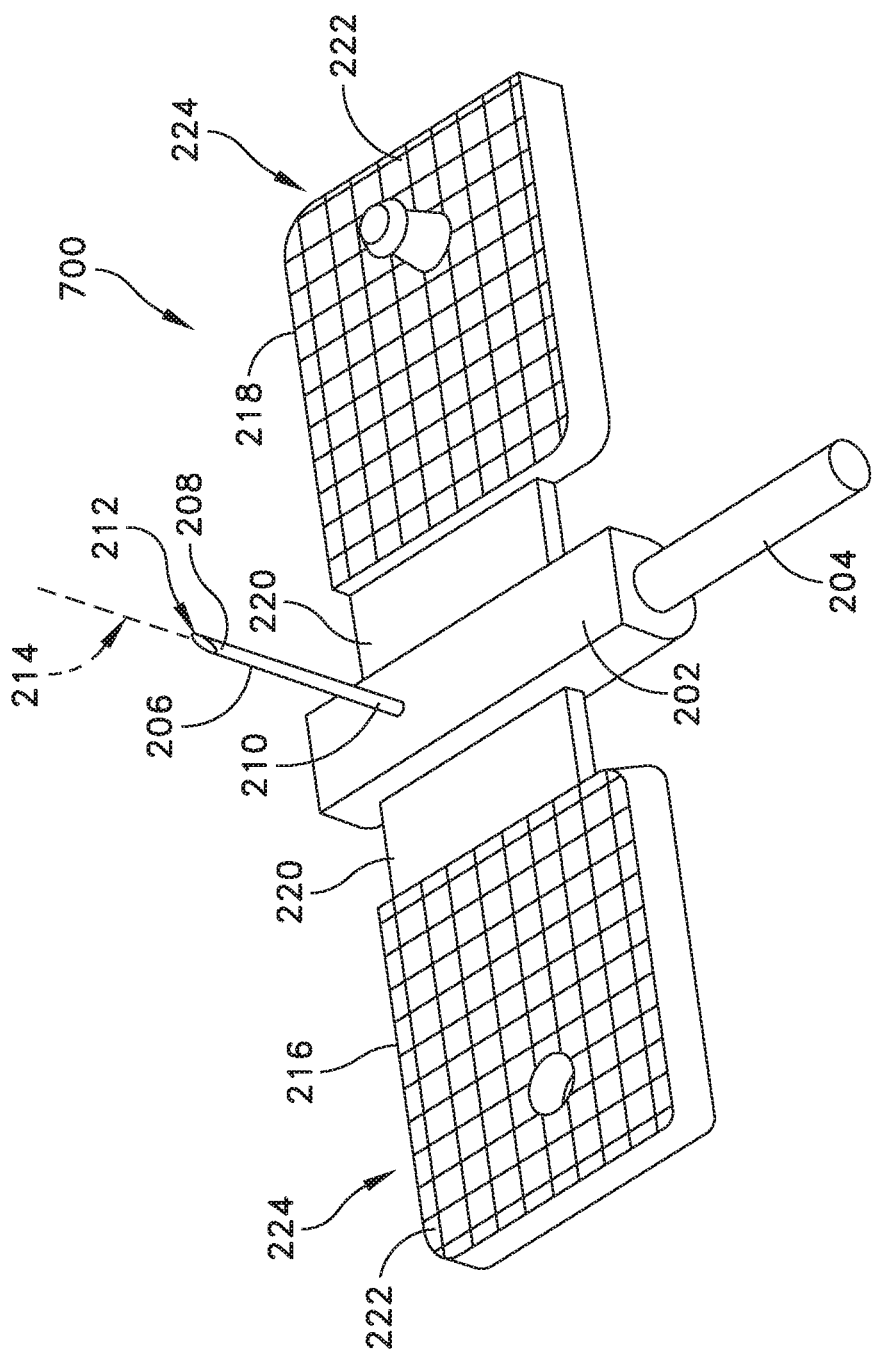
FIG. 7 illustrates a safety device with a mechanical fastener having a rectangular shape.
Figure 8:
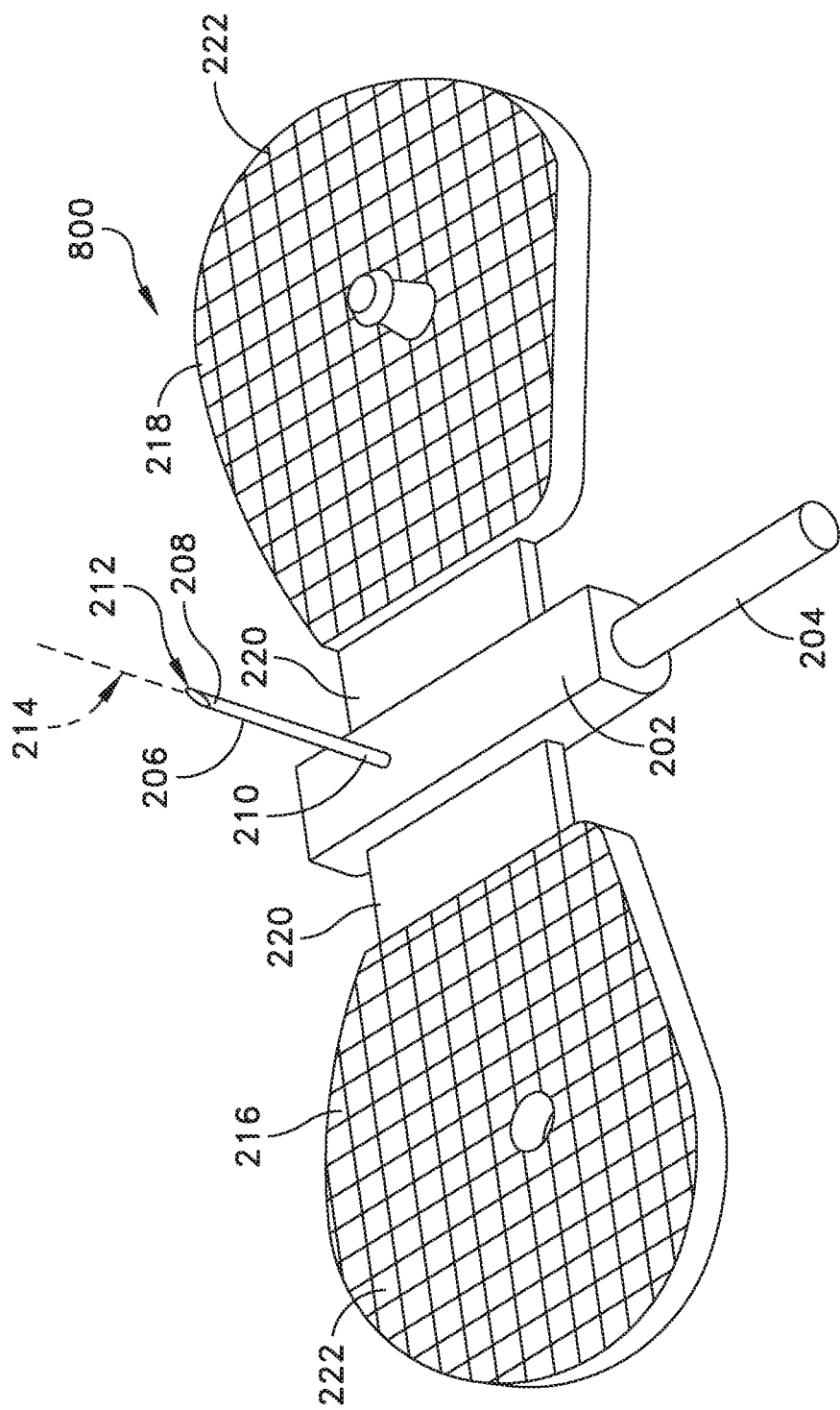
FIG. 8 illustrates a safety device with a mechanical fastener having an elliptical shape.

Wings 216, 218 may have various shapes. For example, device 600 has wings 216, 218 with a circular shape (FIG. 6.) Device 700 has wings 216, 218 with a rectangular shape (FIG. 7.) Device 800 has wings 216, 218 with an elliptical shape (FIG. 8).

Figure 9:
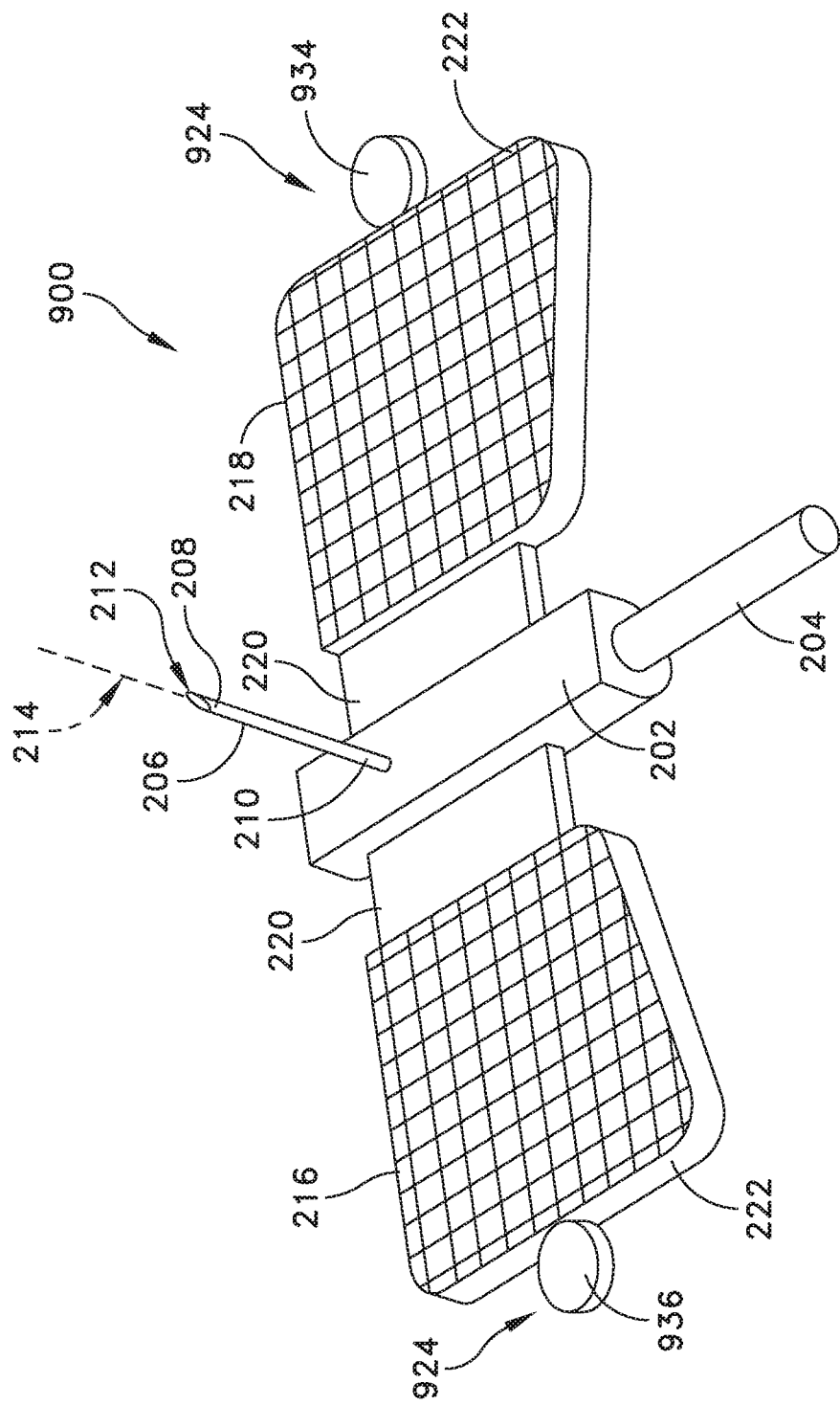
FIG. 9 illustrates a safety device with a mechanical fastener including a first portion and a second portion in attachment to the wings.

A device 900, which is shown in FIG. 9, may include a mechanical fastener 924 with a first portion 934 in attachment to one of the wings 216, 218, and a second portion 936 in attachment to the other one of the wings 216, 218. First portion 934 and second portion 936 may be configured to engage with one another to selectively attach the pair of wings 216, 218 together with medical needle 206 positioned between wings 214, 216. This attachment of the wings 216, 218 protects a user from sharp tip 212 of medical needle 206.

In an embodiment, a device 1000 (FIG. 10) may include a mechanical fastener 1024 with one or both of the wings 216, 218 forming a recessed portion 1038 adjacent a perimeter 1040. Mechanical fastener 1024 may also include a lip 1042 extending from at least a portion of perimeter 1040 of one or both of the wings 216, 218. Recessed portion 1038 and lip 1042 may be configured to engage with one another to selectively attach the pair of wings 216, 218 together with medical needle 206 positioned between wings 216, 218. This attachment of the wings 216, 218 protects a user from sharp tip 212 of medical needle 206.

Figure 37:
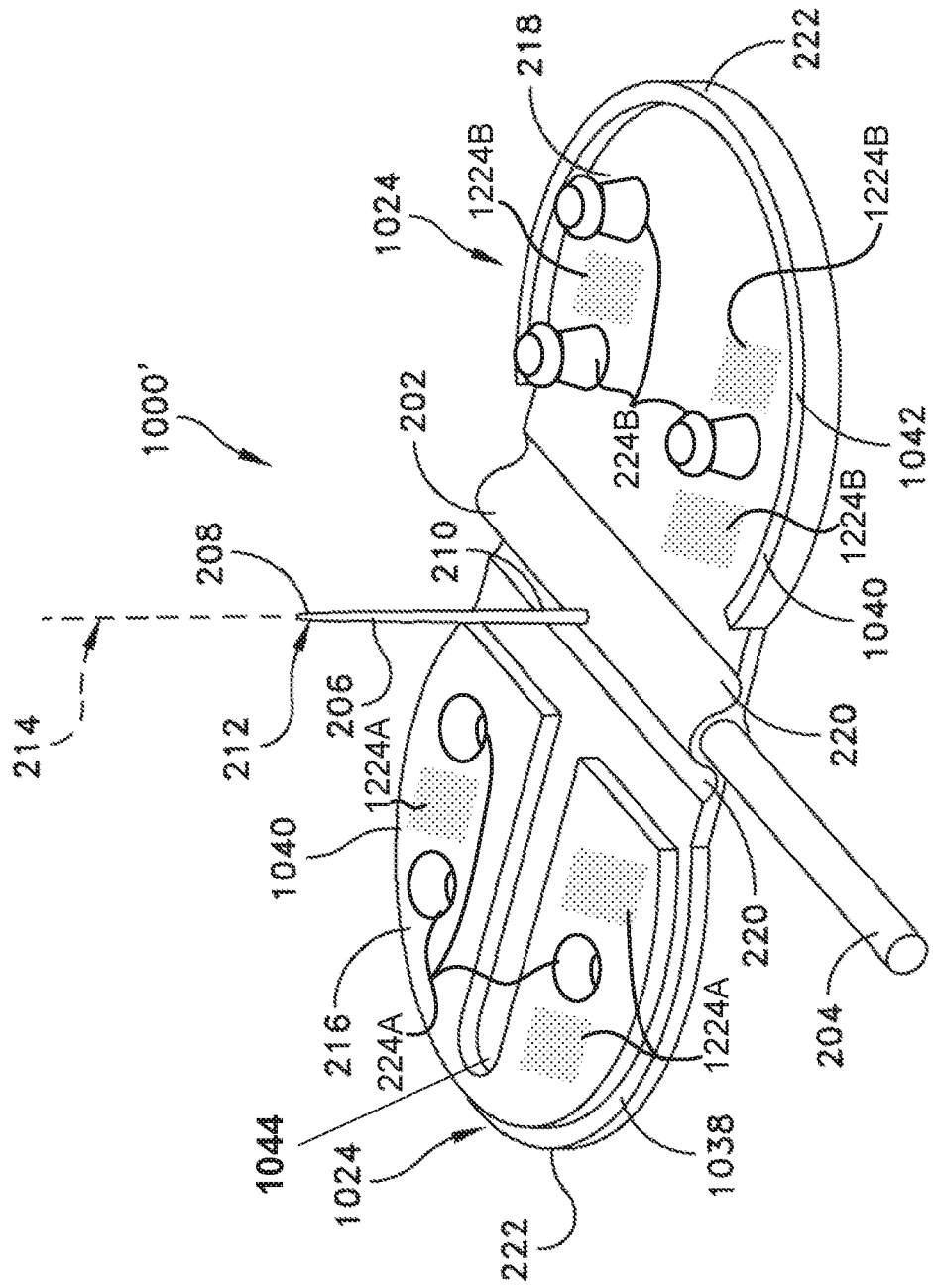
FIG. 37-39 illustrate further embodiments of a safety device with a mechanical fastener in accordance with the invention.

If desired, a device 1000 can include mechanical fasteners in addition to the mechanical fastener 1024. For example, an adhesive and/or hook and loop fastener, or other type of fastener, disclosed herein or otherwise, can be used in addition to the mechanical fastener 1024 of the device 1000. Referring now to FIG. 37, there is shown a device 1000' including the mechanical fastener 1024, as well as additional fasteners, such as mating hook-and-loop fastener portions 1224A and 1224B and/or pins 224B and orifices 224A, as described in connection with FIG. 2. Note that the invention is not intended to be limited only to the embodiments shown herein other variations may be provided without departing from the scope and spirit of the present invention. For example, in addition to the fastener 1024, more or fewer pins and orifices 224A, 224B can be used with or without hook-and-loop fasteners 1224A, 1224B, without departing from the scope of the invention. Alternately, it should be understood that the device 1000' could include the fastener 1024 and the hook-and-loop fasteners 1224A, 1224B, and not the pins and orifices 224A, 224B, if desired. Further, other types of fasteners can be used in addition to the mechanical fastener 1024, such as adhesive and/or snaps 424A and 424B of FIG. 4, in place of, or in addition to, the pins and orifices 224A, 224B and/or the hook-and-loop fastening portions 1224A and 1224B, without departing from the scope of the present invention.

Figure 10:
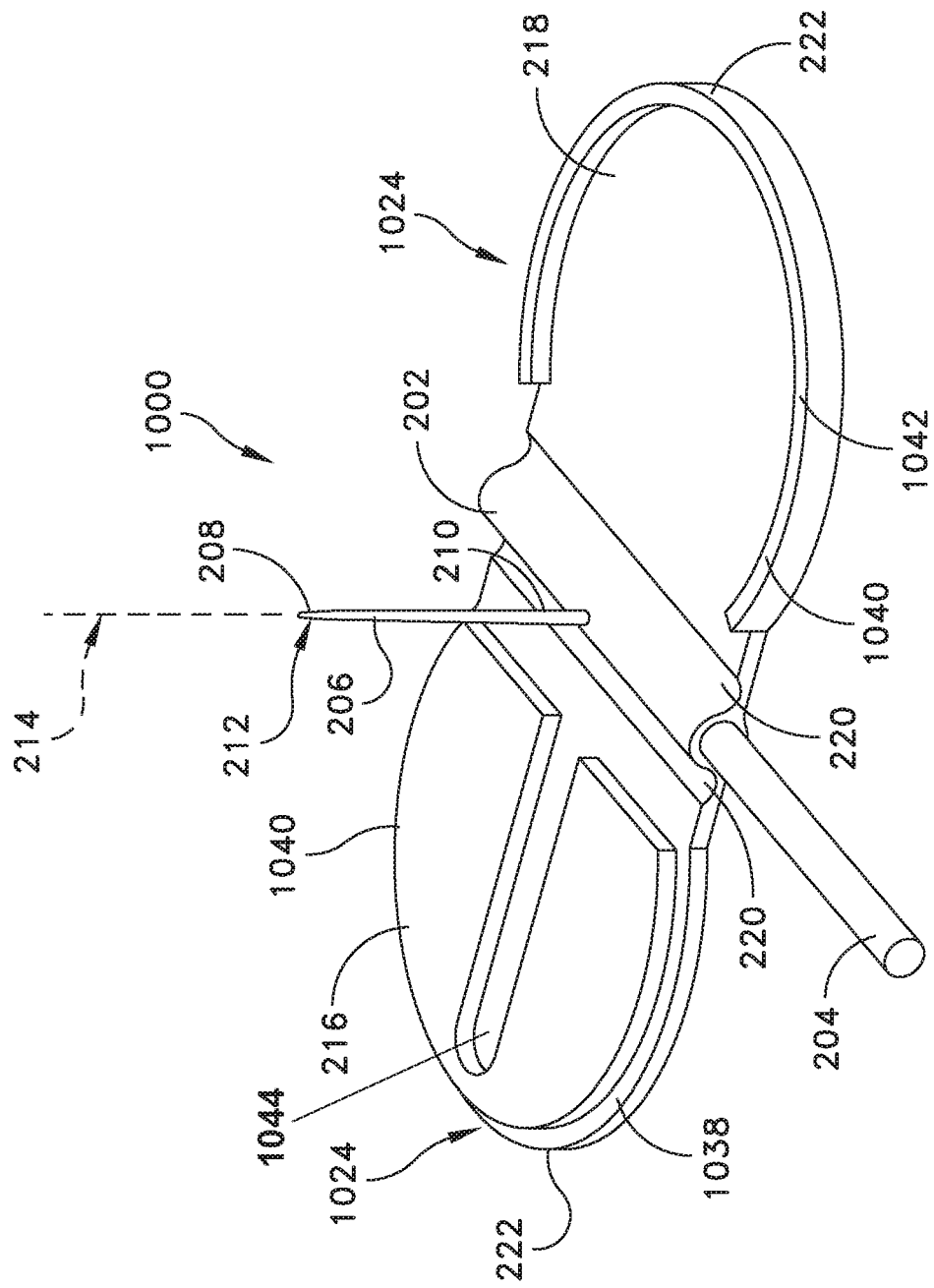
FIG. 10 illustrates a safety device with a mechanical fastener having a lip and a recessed portion configured to engage for attachment with one another, and with a groove sized to house the medical needle.
Figure 38:
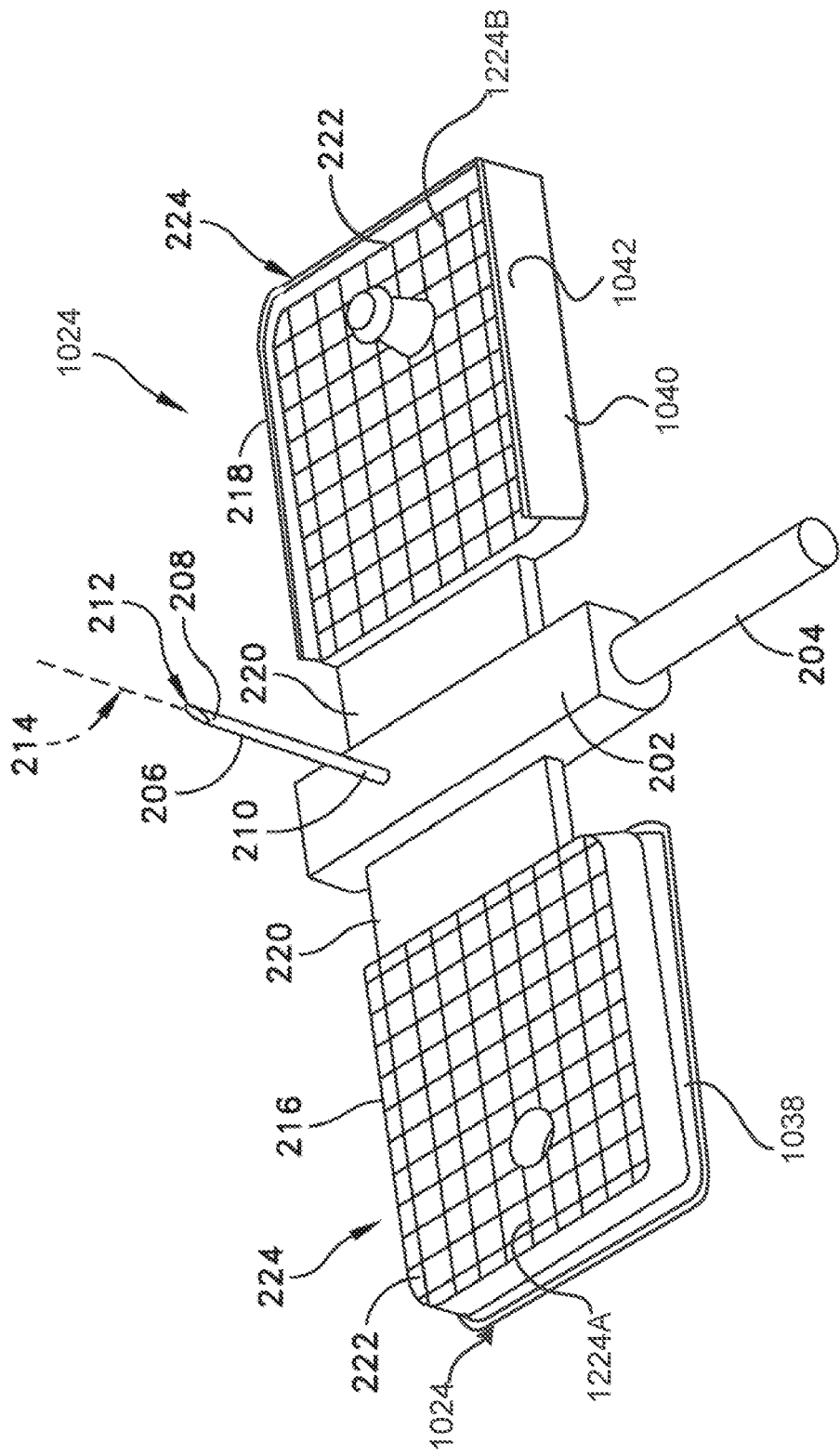
Figure 39:
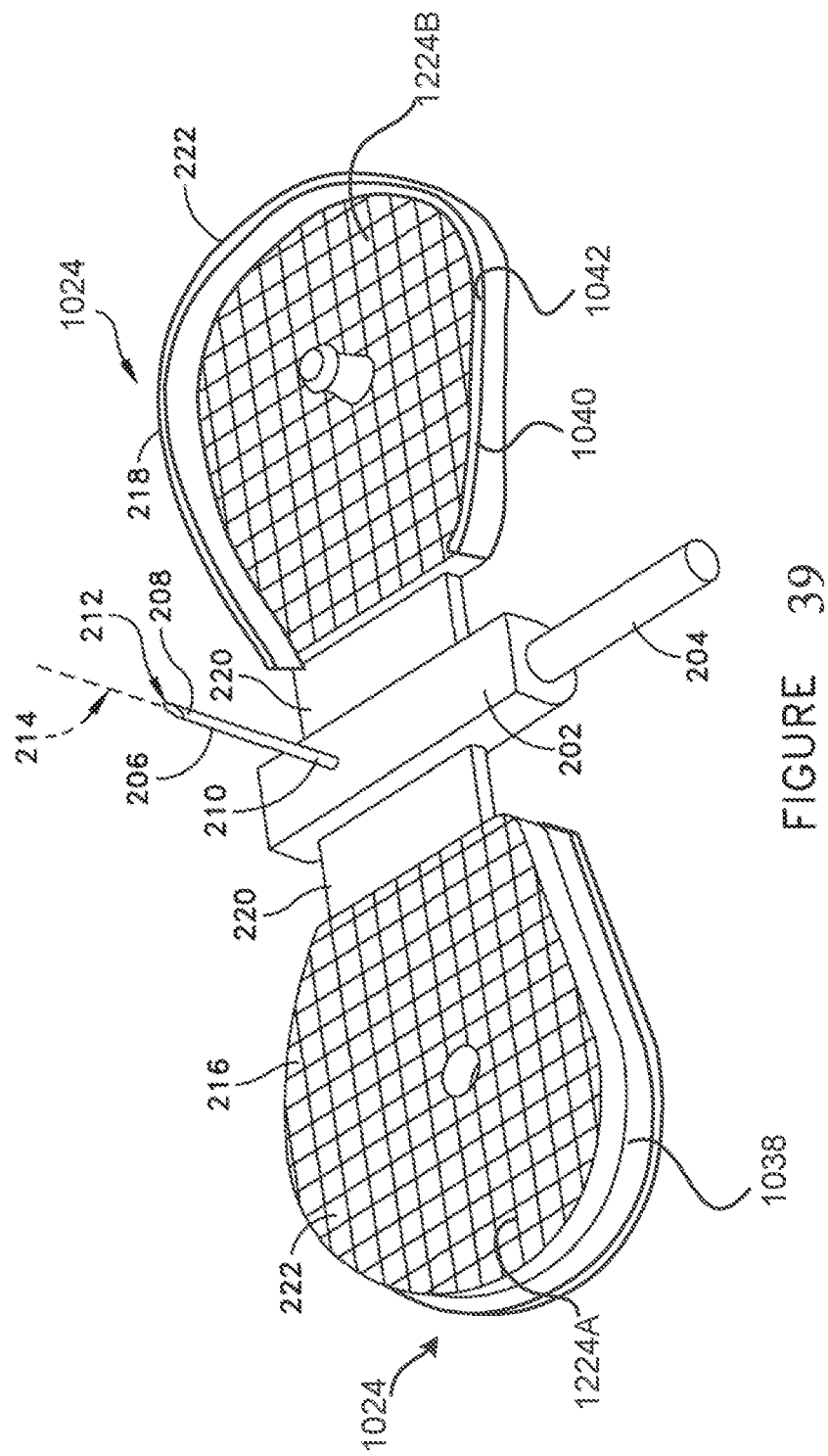

Referring now to FIGS. 10 and 37, in one embodiment, the pair of wings 216, 218 may include rigid material. In another embodiment, the pair of wings 216, 218 may include semi-rigid material. The pair of wings 216, 218 of device 1000, 1000' may be provided in various shapes including, but not limited to, circular shapes and rectangular shapes. See, for example FIGS. 38 and 39, in which other shaped wing designs are shown. Please note that this is not meant to be limiting, as any embodiment of the present invention can be made with differently shaped wings (circles, ellipses, rectangles, trapezoids, etc.), including any other shape desired and/or described herein, without departing from the spirit and scope of the present invention. Additionally, as shown in FIGS. 37-39, one or more types of mechanical fastener (such as pin and orifice, hook-and-loop, adhesive and/or snaps) can be used in addition to the lip and recessed portion fastener 1024, if desired.

Device 1000, 1000' may be provided with a groove 1044 in at least one of the wings 216, 218. Groove 1044 may be sized for housing medical needle 206 after the pair of wings 216, 218 are attached to one another. This attachment of the wings 216, 218 protects a user from sharp tip 212 of medical needle 206. In one embodiment, groove 1044 may be formed in a single one of the wings 216, 218. In another embodiment, groove may be formed in both of the wings 216, 218.

A device 1100 (FIG. 11) provides an exemplary embodiment of handle 1126 extending from central body portion 202. Any of the embodiments disclosed herein may include a handle extending away from central body portion 202 in opposition to medical needle 206 and in a direction from second end 210 to first end 208 of medical needle 206.

Figure 12:
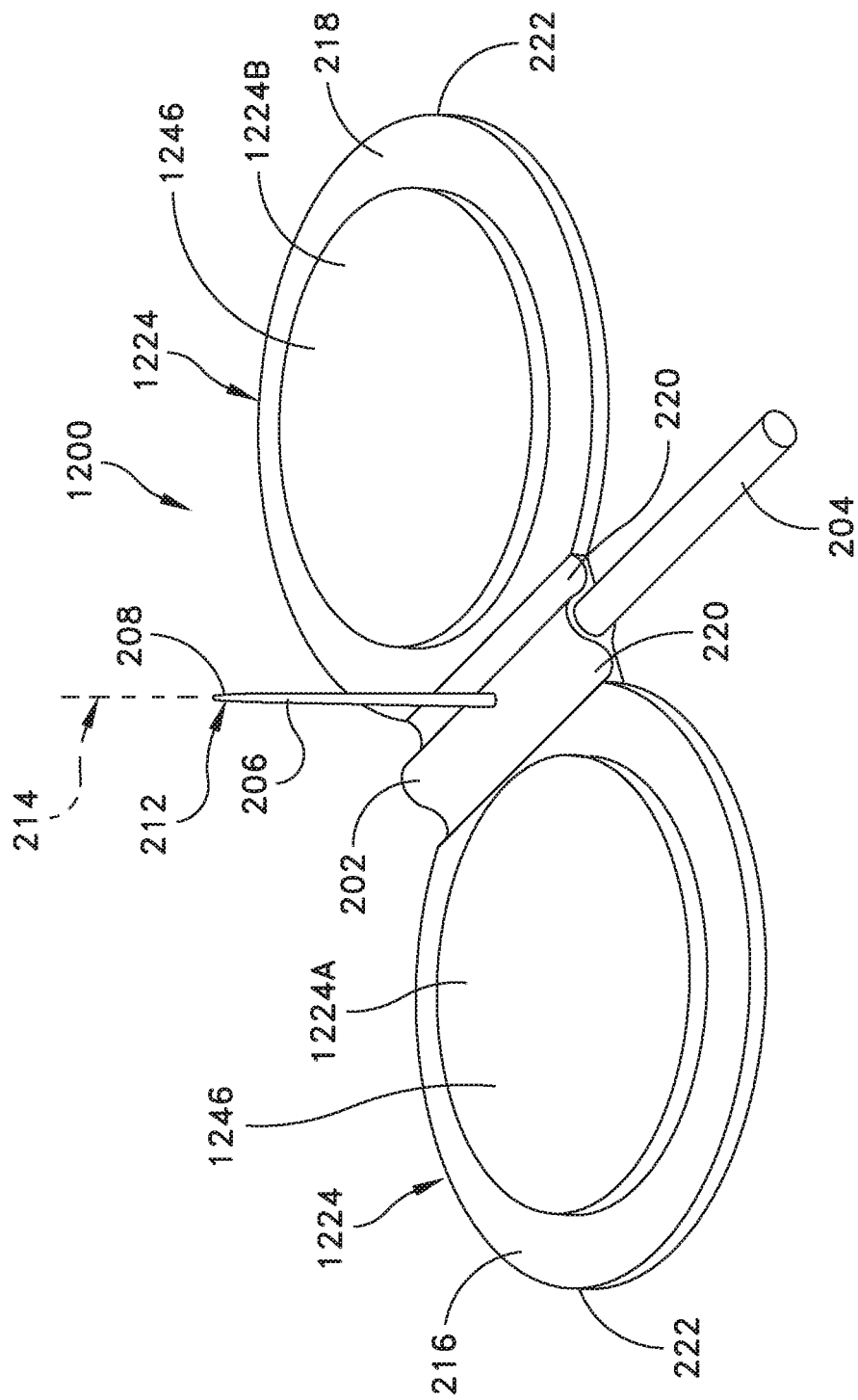
FIG. 12 illustrates a safety device with a mechanical fastener including a hook-and-loop fastening system configured to engage for attachment with one another.

Looking at FIG. 12, and in an embodiment, mechanical fastener 1200 may include a hook-and-loop fastening system 1224 disposed on the pair of wings 216, 218. Hook-and-loop fastening system 1124 may be configured to engage with one another to selectively attach the pair of wings 216, 218 together with medical needle 206 positioned between wings 216, 218. This attachment of the wings 216, 218 protects a user from sharp tip 212 of medical needle 206.

Hook-and-loop fastening system 1224 may include a hook material 1224A disposed on one of the wings 216, 218. A loop material 1224B may be disposed on the other one of the wings 216, 218. Hook material 1224A and loop material 1224B may be configured to engage with one another to selectively attach the pair of wings 216, 218 together with medical needle 206 positioned between wings 216, 218. This attachment of the wings 216, 218 protects a user from sharp tip 212 of medical needle 206.

Figure 13:
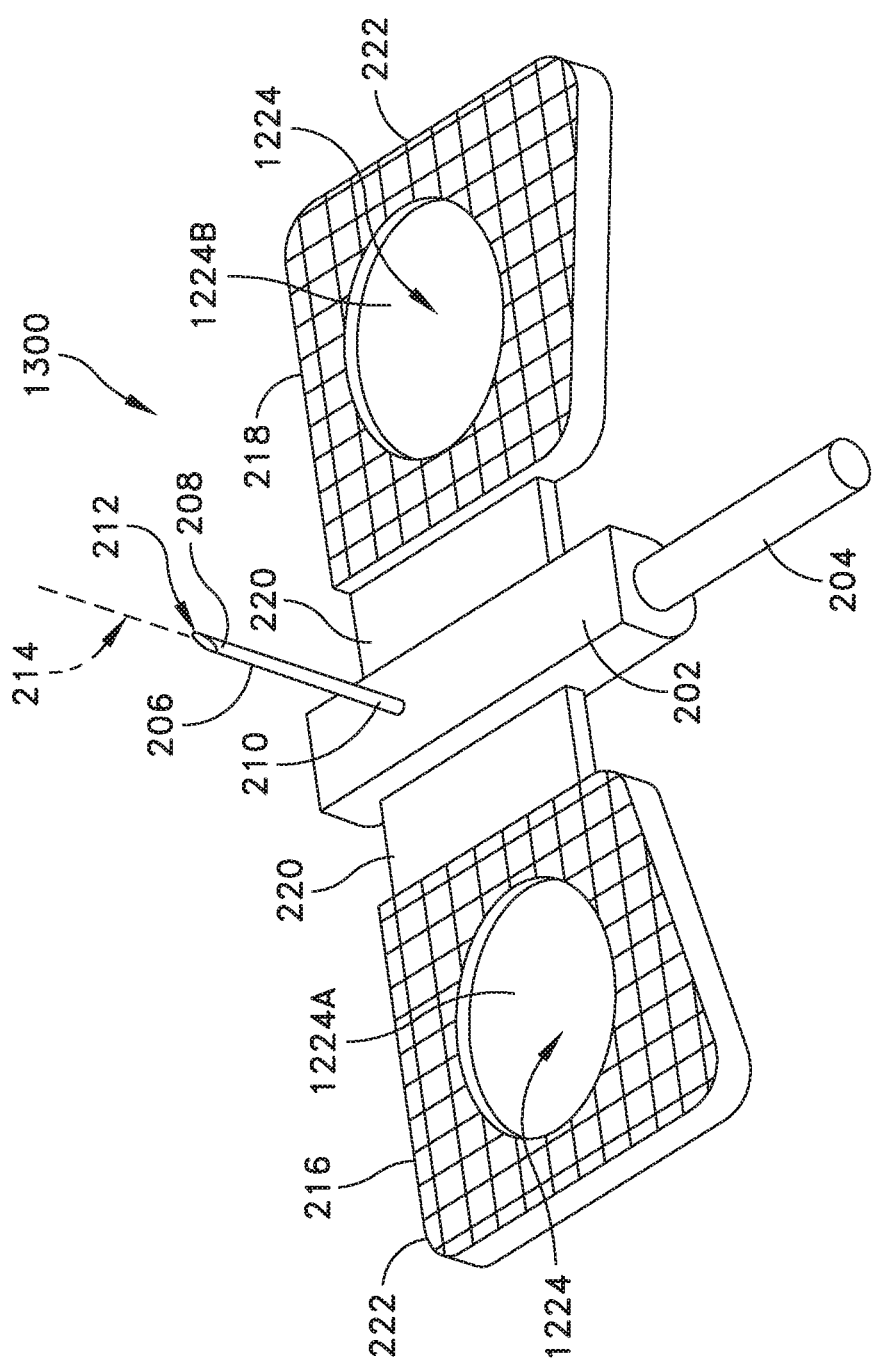
FIG. 13 illustrates a safety device with a hook-and-loop fastening system configured with low profile hook material and low-profile loop material.

Referring to FIG. 13, and in one embodiment, device 1300 may provide hook-and-loop fastening system 1224 with hook material 1224A having a low profile together with loop material 1224B having a low profile.

Referring back to FIG. 12, hook-and-loop fastening system 1224 may also include hook material 1224A and loop material 1224B on each of the pair of wings 216, 218. Hook material 1224A and loop material 1224B may be disposed for engagement with one another on opposed wings 216, 218. This configuration of hook material 1224A and loop material 1224B provides a dual locking configuration.

In an embodiment, hook-and-loop fastening system 1224 may include hook material 1224A on one of the wings 216, 218, loop material 1224B on the other one of the pair of wings 216, 218, and adhesive material 1246 within one or both of hook material 1224A and loop material 1224B. Adhesive material 1246 in hook material 1224A and loop material 1224B may be disposed for engagement with one another to attach the pair of wings 216, 218 together with medical needle 206 positioned between wings 216, 218. This attachment of the wings 216, 218 protects a user from sharp tip 212 of medical needle 206.

In various embodiments, wings 216, 218 may be configured with various materials and in various shapes. For example, wings 216, 218 of device 1200 may include rigid material. Wings 216, 218 of device 1200 may include semi-rigid material. Wings 216, 218 of device 1200 may include soft material. Wings 216, 218 of device 1200 may include gel material. Wings 216, 218 of device 1200 may include cloth. Wings 216, 218 of device 1200 may include non-woven cloth. In addition, the pair of wings 216, 218 may include a combination of a rigid material, a semi-rigid material, a soft material, a gel material, a cloth material, and a non-woven cloth material. Wings 216, 218 of device 1200 may have one or more shapes, including, for example, a circular shape, a rectangular shape.

In an embodiment, adhesive material 1246 may be dynamically activated. Dynamic bonding agents may include a two-component glue-primer and glue each applied to one of the two surfaces to be bonded in which neither component is active until contact with one another. In an alternative example, a "bubble" full of instant glue, which may have a response time of under three seconds, may be configured to burst upon pressing wings 216, 218 together.

Adhesive material 1246 may be incorporated in a gel carrier. A gel carrier is a good way to house a bubble of the instant glue above. Gel or silicone are a very comfortable materials for patients and can overlay hypo-allergenic double-sided adhesive tapes. This may facilitate attachment of the device to the patient's skin.

Figure 14:
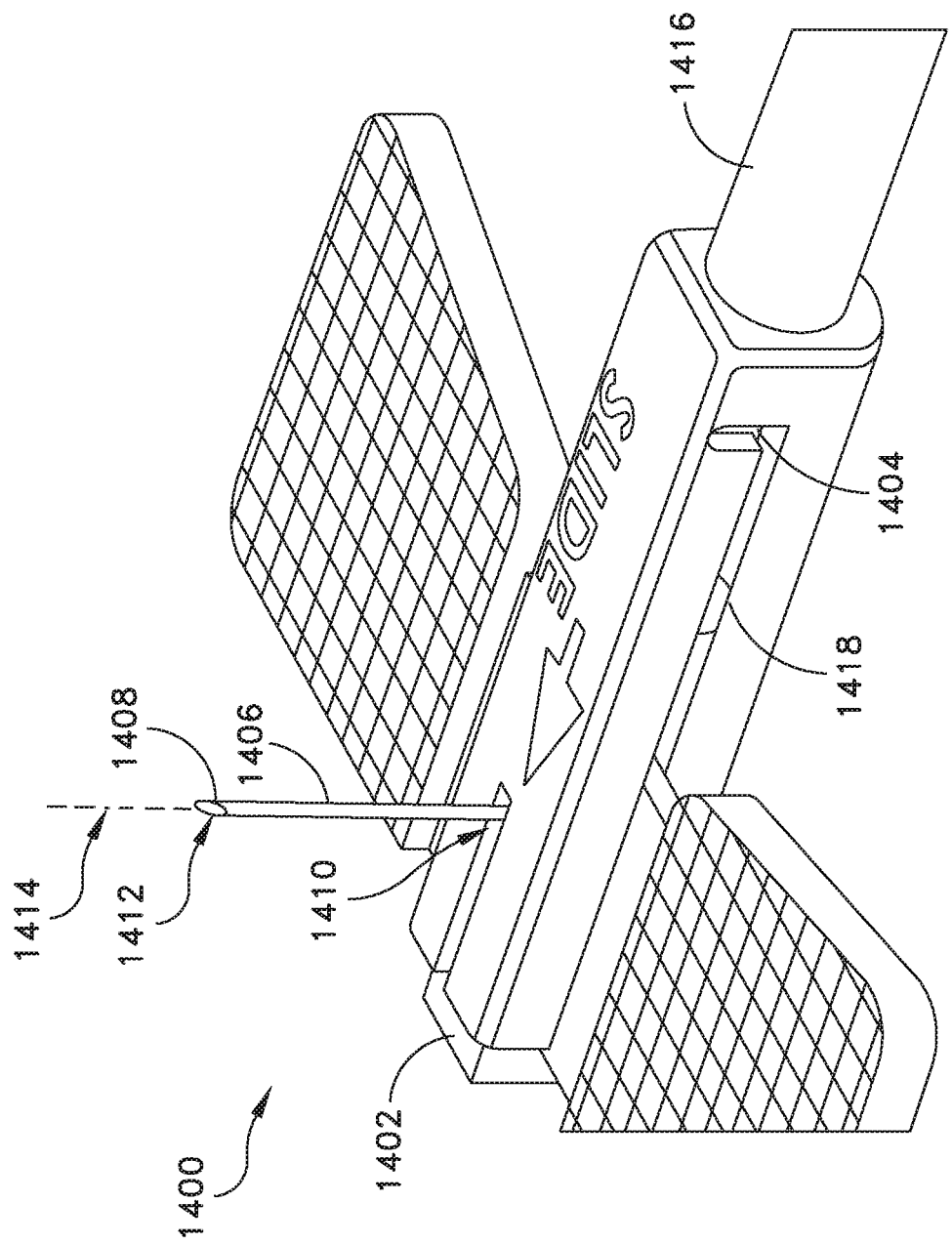
FIG. 14 illustrates a safety device with a sleeve having a sliding mechanism to selectively cover medical needle.
Figure 15:
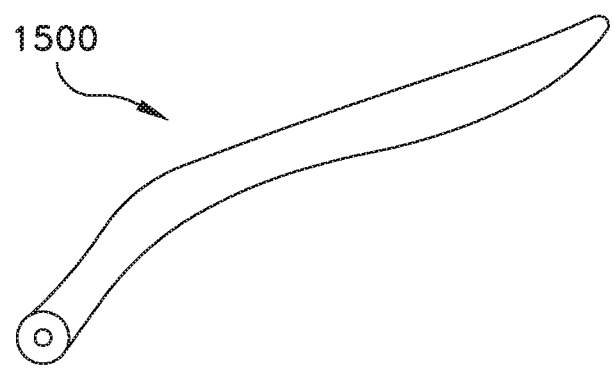
FIG. 15 illustrates non-DEHP tubing for use with a needle protection device.

Referring now to FIG. 14, and in an embodiment, a device 1400 is provided to protect a user from sharp tip of medical needle. Device 1400 may include a central body portion 1402 in fluid connection with a delivery tube 1404.

A medical needle 1406 may be provided with a first end 1408 and a second end 1410 in opposition to one another. First end 1408 may be in fluid connection with central body portion 1402 and delivery tube 1404. Second end 1410 of needle 1406 may extending away from central body portion 1402 to a sharp tip 1412. A line from first end 1408 to second end 1410 of medical needle 1406 defines a longitudinal axis 1414.

A sleeve 1416 may be slidably disposed in a surrounding configuration to central body portion 1402. A sliding mechanism 1418 (e.g., grooves 1418) may formed by sleeve 1416 and central body portion 1402 to allow movement of sleeve 1416 from a first position to a second position.

In the first position, sleeve 1416 may provide medical needle 1416 in a configuration for insertion into a patient and delivery of a medicinal fluid in the patient (i.e., needle 1406 is substantially perpendicular to delivery tube 1404.) In the second position, sleeve 1416 may cover medical needle 1406 so as to protect a user from sharp tip 1412 of medical needle 1406 (i.e., needle 1406 is substantially parallel to delivery tube 1404).

Figure 16:
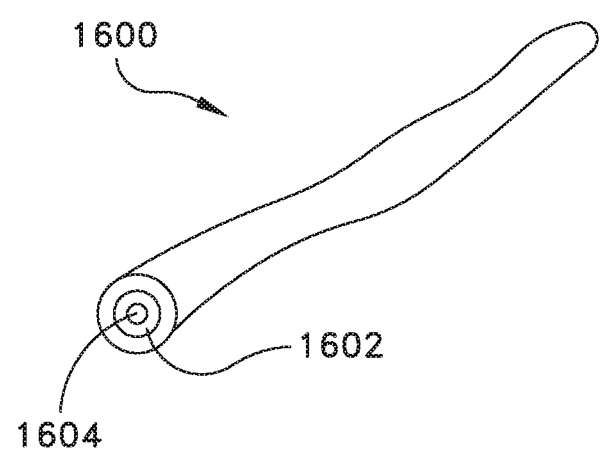
FIG. 16 illustrates a section of polypropylene lined tubing with a layer of polypropylene surrounding an inner lumen for use with a needle protection device.

In one embodiment, needle safety devices may be provided non-DEHP tubing 1500 (FIG. 15) or polypropylene lined tubing 1600 (FIG. 16) with a layer 1602 of polypropylene surrounding an inner lumen 1604. Most needle safety devices may be built with a non-DEHP tubing. Polypropylene is a means to minimize chemical interaction (i.e., between the drug and the plastic, thus, minimizing the bleaching effect). Devices may be provided with two tubing material options to minimize chemical interchange with drug. One of these options may include non-DEHP tubing. Another option is polyethylene lined tubing, which provides the least interaction with infused drug.

Figure 17:
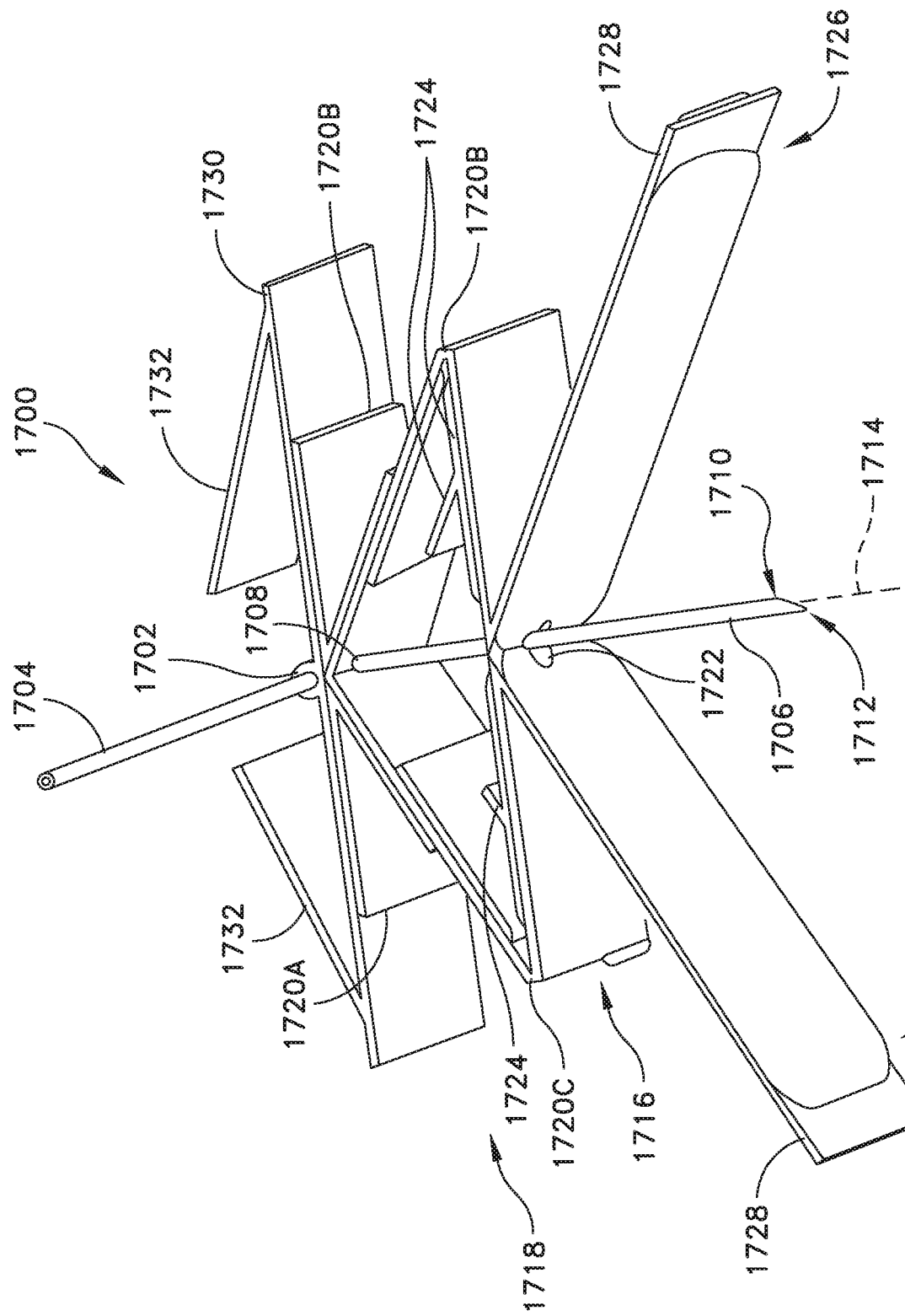
FIGS. 17 and 18 illustrate exemplary embodiments of a frame member with a polygonal structure selectively positionable to cover medical needle.
Figure 18:
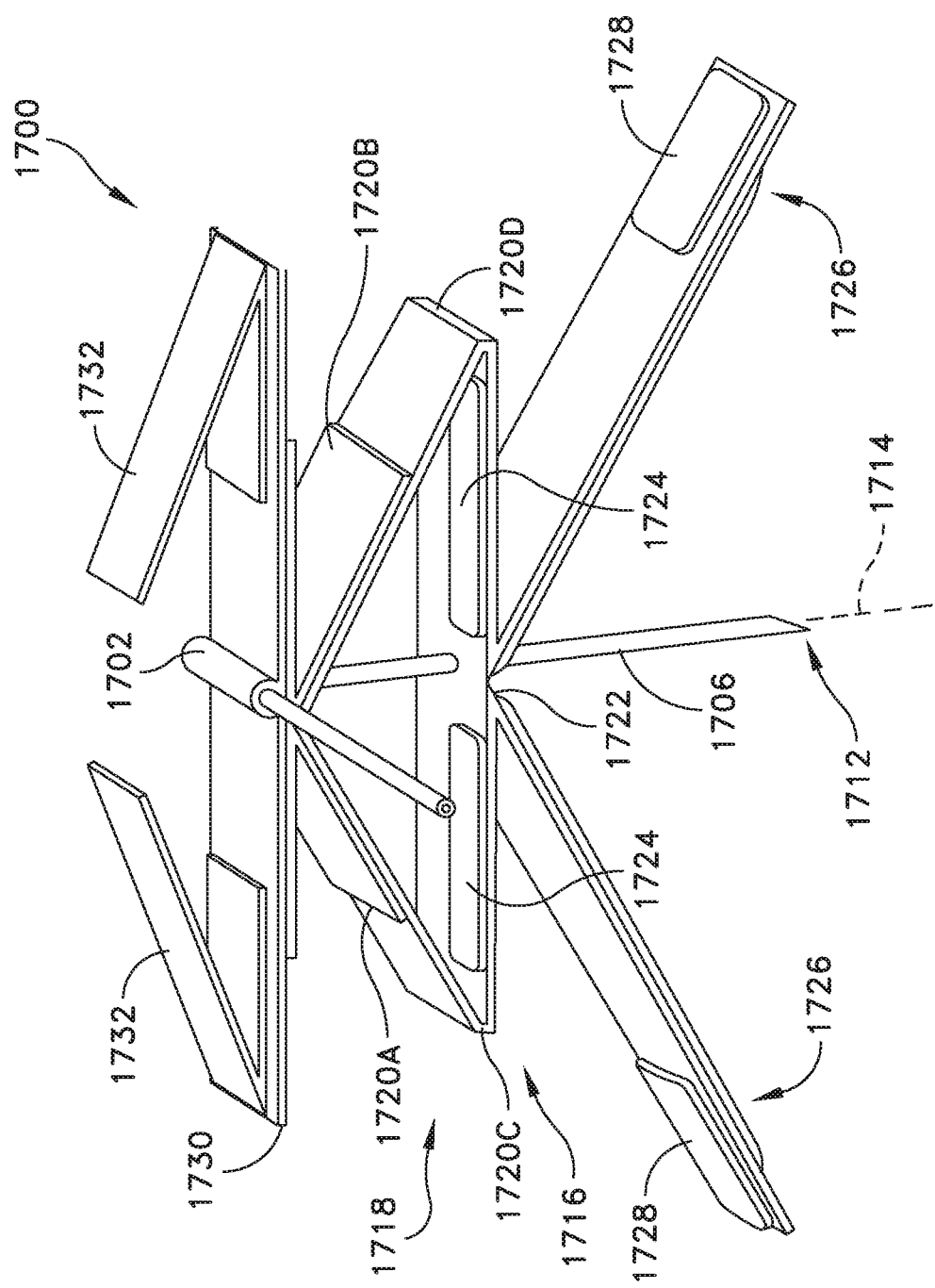

Referring to FIGS. 17-18, and in an embodiment, a device 1700 is provided for protecting a user from a sharp tip of a medical needle. Device 1700 includes a central body portion 1702 in fluid connection with a delivery tube 1704. A medical needle 1706 has a first end 1708 and a second end 1710 in opposition to one another. First end 1708 may be in fluid connection with central body portion 1702 and delivery tube 1704. Second end 1710 of needle 1706 extends away from central body portion 1702 to a sharp tip 1712. A line from first end 1708 to second end 1710 of medical needle 1706 defines a longitudinal axis 1714.

Device 1700 includes a frame member 1716 forming a polygonal structure 1718 extending from central body portion 1702. Polygonal structure 1718 has a first hinged portion 1720A, a second hinged portion 1720B, a third hinged portion 1720C, and a fourth hinged portion 1720D. First hinged portion 1720A and second hinged portion 1720C may be positioned at central body portion 1720. First hinged portion 1720A and second hinged portion 1720B may be positioned in opposition to one another. Third hinged portion 1720C and fourth hinged portion 1720D may be positioned in opposition to one another and extend from first hinged portion 1720A and second hinged portion 1720B. Polygonal structure 1718 may form an opening 1722 at second hinged portion 1720B sized for passage of medical needle 1706.

Polygonal structure 1718 may be selectively positionable from a first position to a second position. First position 1718 may be configured with each of first hinged portion 1720A and second hinged portion 1720B in a closed configuration, and third hinged portion 1720C and fourth hinged portion 1720D in a closed configuration. For insertion into patient, 1720A and 1720B are typically in an open position, which allows wings 1730 to serve as the handle and device to insert the needle while third hinged portion 1720C and fourth hinged portion 1720D are in the closed position with layer 1726 lying flat against mechanical fasteners 1724 In this configuration, medical needle 1706 is extended through opening 1722 for placement into a patient and delivery of a medicinal fluid. After insertion, mechanical fastener portions 1732 are laid over base portion 1728 (mechanical fastener portions 1732 and base portion 1728 may have hook-and-loop fastener portions on both sides) to secure the overall device in place. Prior to removal, fastener portions 1732 are removed from base portion 1728, then the clinician's hand (left or right depending on preference) is placed over layer 1726 but not over any other layer and first hinged portion 1720A and second hinged portion 1720B are moved to an open position to allow for the needle to be pulled out thus bringing third hinged portion 1720C and fourth hinged portion 1720D to a closed position. Second position may be configured with first hinged portion 1720A and second hinged portion 1720B in an open configuration, and third hinged portion 1720C and fourth hinged portion 1720D in an open configuration. In this configuration, medical needle 1706 is withdrawn through opening 1722 and polygonal structure 1718 is closed around medical needle 1706. This surrounding configuration of polygonal structure 1718 around medical needle 1706 protects a user from sharp tip 1712.

In an embodiment, one or more mechanical fasteners 1724 may be disposed on frame 1716. Mechanical fastener 1724 may be configured to selectively attach opposed areas of portions 1720C and 1720D to one another with medical needle 1706 positioned between opposed ones of portion 1720A and 1720B, and portion 1720C and 1720D. This surrounding configuration of polygonal structure 1718 around medical needle 1706 protects a user from sharp tip 1712.

In one embodiment, one or more mechanical fasteners 1724 may include a hook-and-loop fastening system. The hook-and-loop fastening system may include a hook material having a low profile as well as a loop material having a low profile. In an embodiment, the hook-and-loop fastening system may include a hook material and a loop material on each of the regions 1724 between third hinged portion 1720C and fourth hinged portion 1720D. The hook material and the loop material may be disposed to engage with one another so as to provide a dual locking configuration.

Mechanical fastener 1724 may include an adhesive material disposed on one or more of portion 1720C and 1720D. The adhesive material may be configured to engage with another area of portions 1720C and 1720D of polygonal structure 1718 to selectively attach opposed portions 1720C and 1720D of polygonal structure 1718 to one another with medical needle 1706 positioned between opposed portions 1720A, 1720B, 1720C, and 1720D. This surrounding configuration of polygonal structure 1718 around medical needle 1706 protects a user from sharp tip 1712.

In an embodiment, the adhesive material may be dynamically activated. The adhesive material may optionally be incorporated in a gel carrier. In various embodiments, mechanical fastener 1724 may include peelable coverings containing adhesive.

Opposed portions 1720A, 1720B, 1720C, and 1720D of polygonal structure 1718 may be shaped in a variety of shapes, which include, but are not limited to a circular shape, a rectangular shape, and an elliptical shape. Opposed portions 1720A and 1724B as well as 1720C and 1720D of polygonal structure 1718 may include rigid material, semi-rigid material, soft material, gel material, cloth, non-woven cloth, or a combination of these materials.

In an embodiment, an adhesive layer 1726 may extend from central body portion 1702.

Handle 1730 may extend away from central body portion 1702 in opposition to medical needle 1706 and in a direction from first end 1708 to second end 1710 of medical needle 1706. Handle 1730, or any of the handles described hereinabove, facilitates the manipulation of the device during removal. Handle 1730 may be shaped as a tab, a loop, with flaps or wings, or as a detachable clip. Handle 1730 may include rigid material, semi-rigid material, soft material, gel material, cloth, non-woven cloth, or a combination of these materials. Handle 1730 allows the user to remove device 1700 by providing a grab portion to be pulled upwardly. Handle 1730 may include a mechanical fastener 1732 (for example, hook-and-loop material 1732) that mates with base portion 1728. In an embodiment, a mechanical fastener 1732 may extend from base 1728. Handle 1730 and mechanical fastener 1732 may be used to maintain device 1700 in a relatively flat configuration and are generally not attached to a patient. Mechanical fastener 1732 may be configured to removably attach to a patient.

Various methods of protecting a user from a sharp tip of a medical needle are provided by the present invention. In one exemplary embodiment, a method of protecting a user from a sharp tip of a medical needle includes withdrawing a sharp tip of a medical needle from a patient. The method further includes closing a pair of wings with the medical needle positioned between the wings. The method also includes fastening the pair of wings together with the medical needle positioned between the wings. This protects a user from the sharp tip of the medical needle.

In another exemplary embodiment, a method of protecting a user from a sharp tip of a medical needle includes withdrawing a sharp tip of a medical needle from a patient. The method also includes sliding a sleeve slidably disposed in a surrounding configuration to a central body portion from a first position providing the medical needle in a configuration for insertion into the patient and delivery of a medicinal fluid in the patient to a second position covering the medical needle. This protects a user from the sharp tip of the medical needle.

In an embodiment, a method of protecting a user from a sharp tip of a medical needle includes withdrawing a sharp tip of a medical needle from a patient through an opening formed in a polygonal structure of frame member. The method further includes articulating hinges of the polygonal structure to close the frame member surrounding the medical needle. This protects a user from the sharp tip of the medical needle.

Most of the safety devices may be configured with a low profile and small footprint. A small footprint is particularly useful when the implanted port is a dual port that can only be accessed by two needle sets with a small footprint. Selected materials and a low profile provide enhanced patient comfort, ease of manipulation, ease of fixation, and reduced number of separate pieces to be used when the device is put on the patient.

A misaligned orifice may be provided in device 1700 by providing a non-concentric needle axis through orifice 1722. Needle 1706 is forced to fit through orifice 1722 during assembly of the device. Once the needle is pulled through orifice 1722, its axis will force it to its natural position and, thus, it will not be in alignment with orifice 1722. In one embodiment, the orifice through which the needle goes through on a lower wing can be purposely misaligned (e.g., about twice as much as the needle diameter) so that when the needle is pulled and the double wings take a diamond shape that gradually flattens; the needle will shift out of alignment with the hole.

In an embodiment, a hook-and-loop material 1734 may be positioned on the lower side of wings 1730 and the upper part of frame member 1716. When the needle is in the patient and the device is flat against the skin, hook-and-loop material 1732 secures the device in its flat position. The loop is the simplest of the three options to be able to pull up the entire polygonal structure. Removal may also be accomplished by pulling on a tab or wings 1730.

Figure 19:
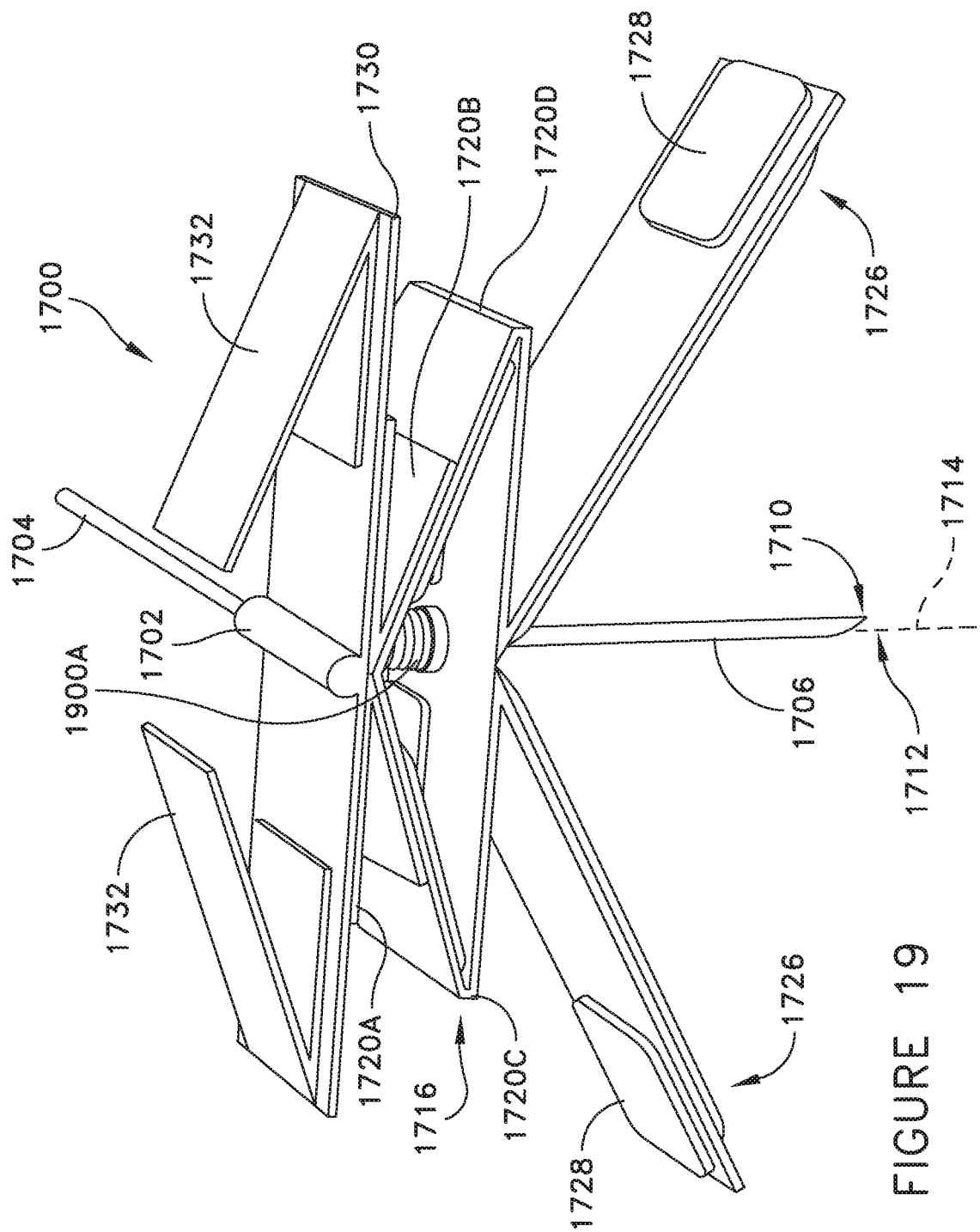
FIGS. 19-21 illustrate a frame member with a cylindrical shroud within a polygonal structure selectively positionable to cover medical needle.
Figure 20:
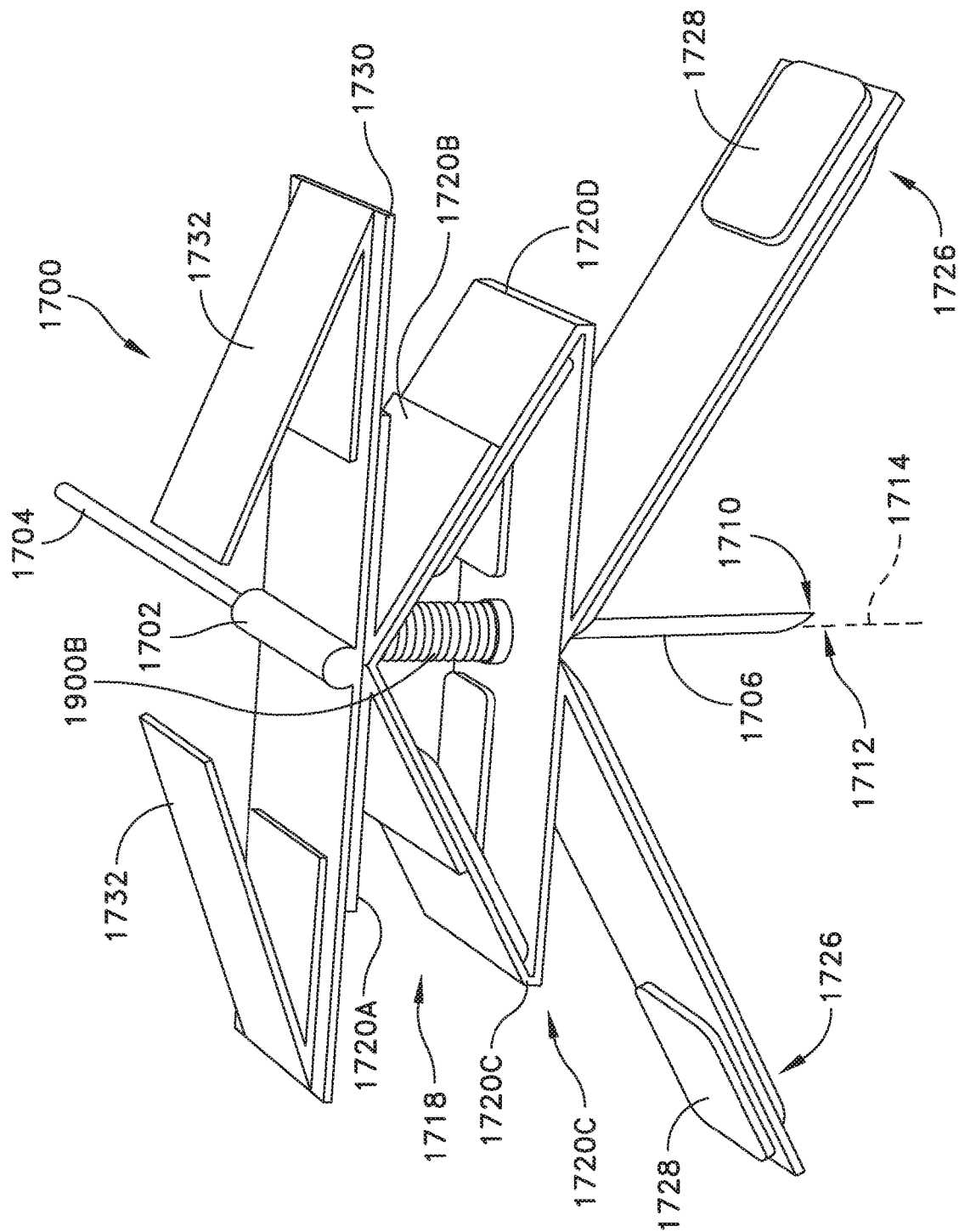
Figure 21:
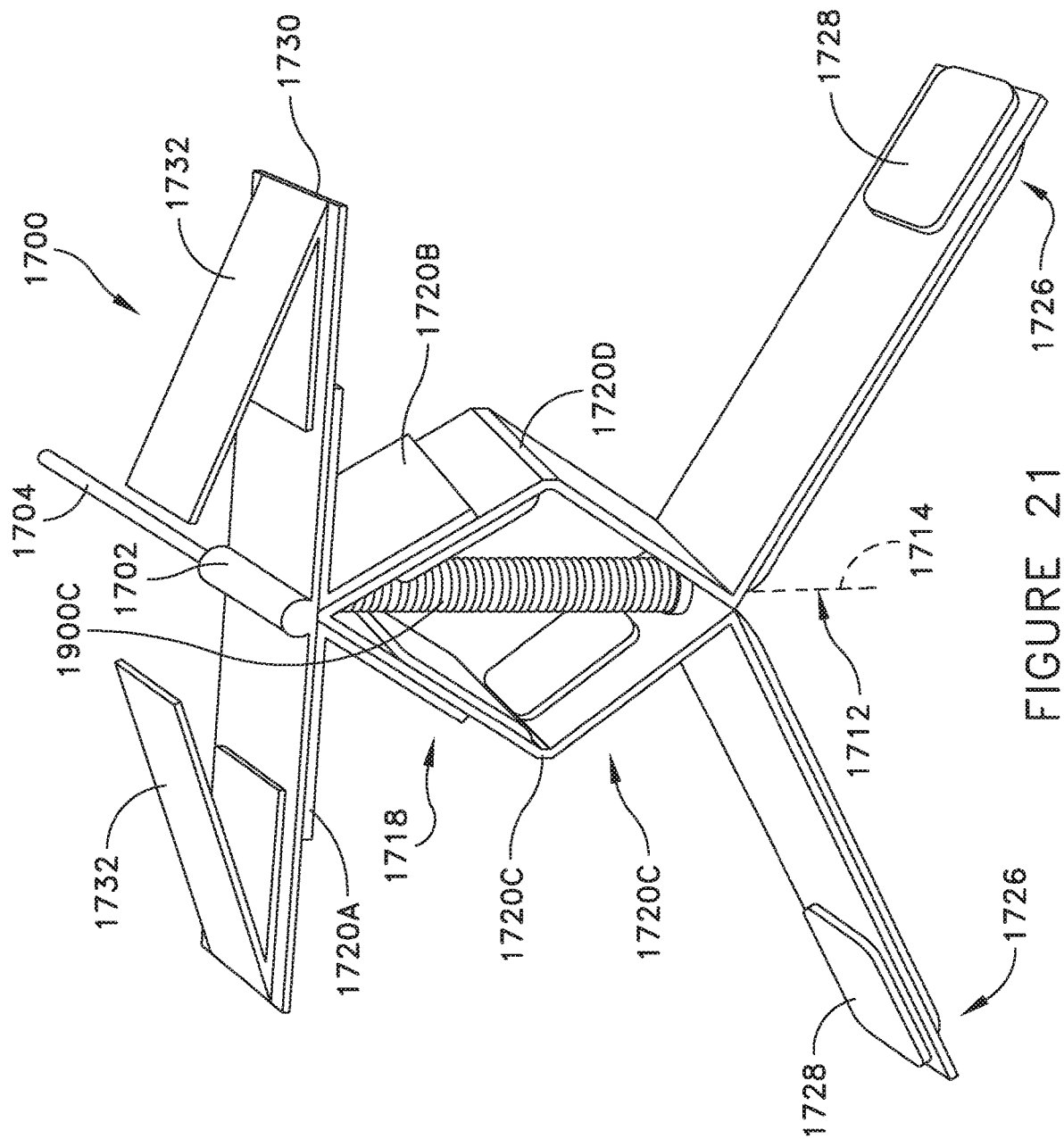
Figure 22:
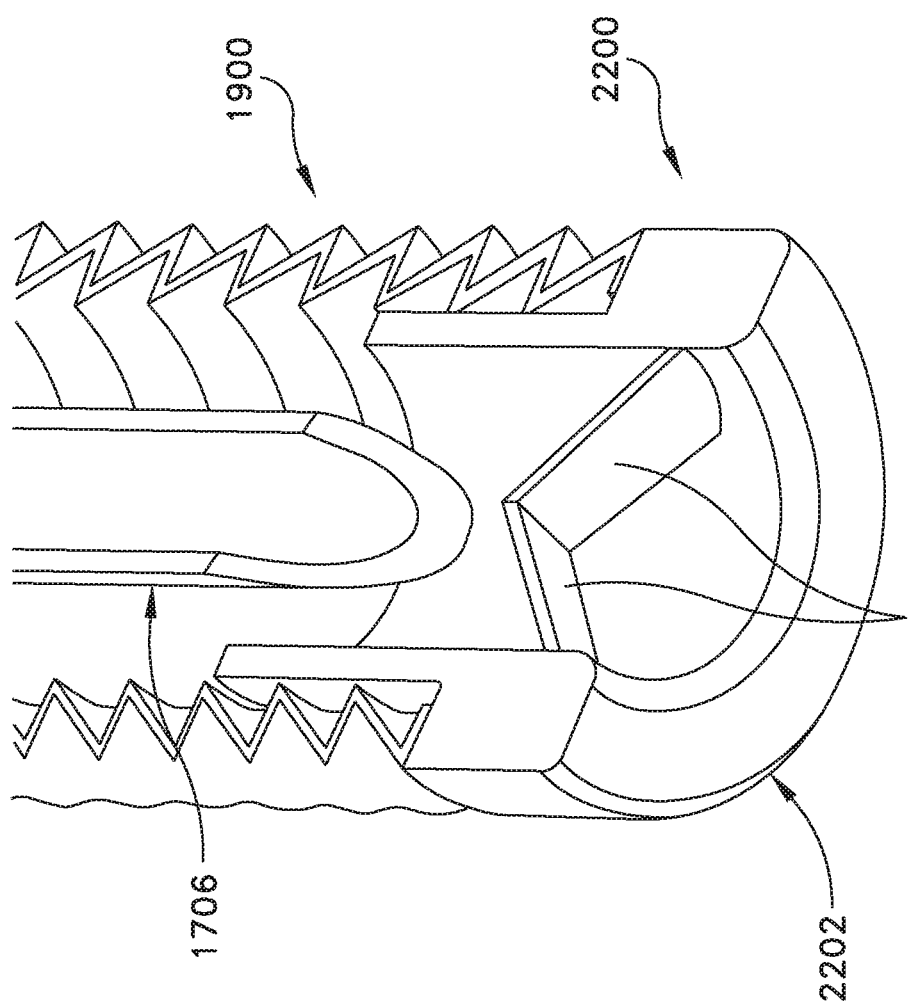
FIGS. 22-25 illustrate a needle trap at the distal end of a shroud, such as the one shown in FIGS. 19-21.
Figure 23:
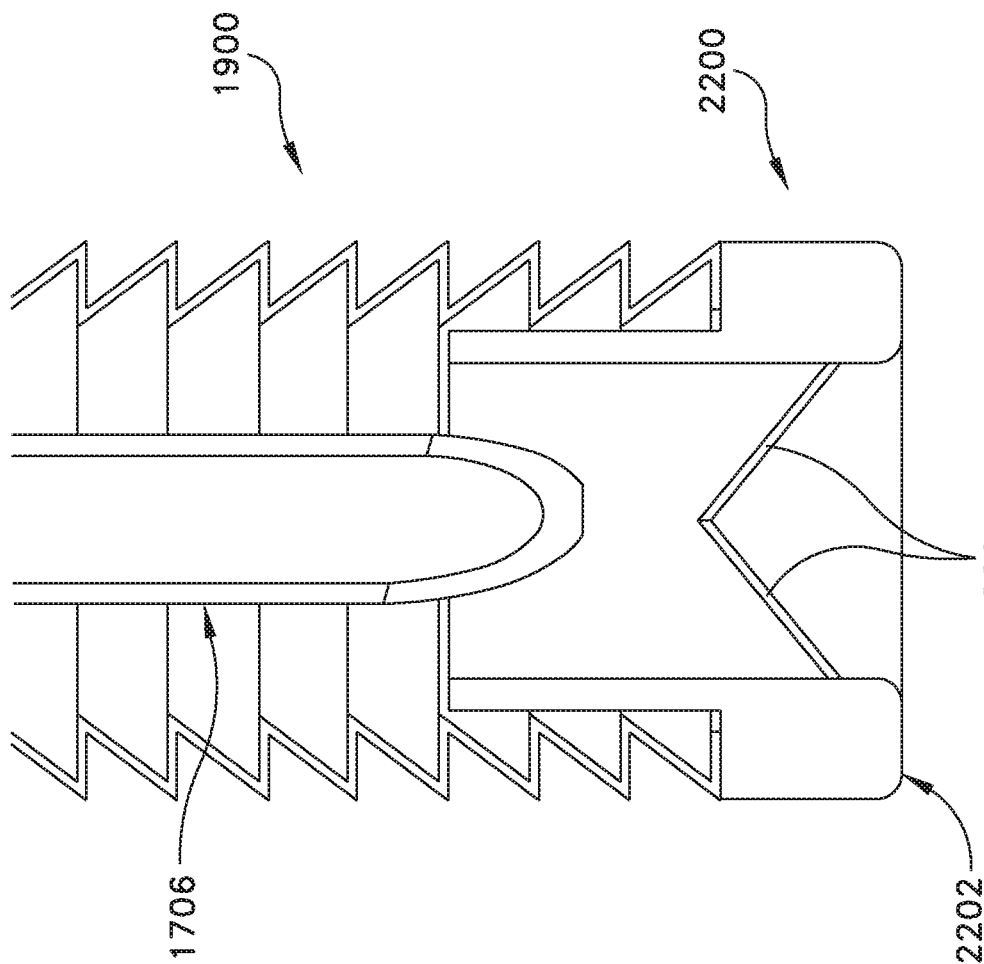
Figure 25:
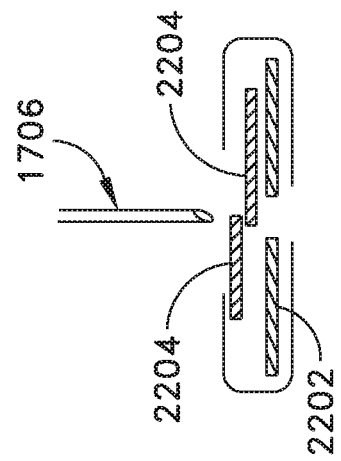
Figure 24:
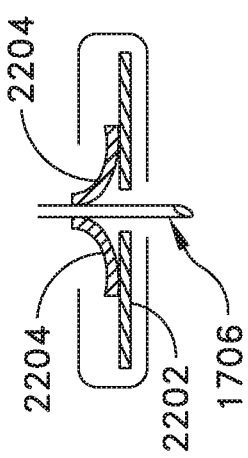

In an embodiment, there may be a shroud 1900 positioned between hinged portions 1720A-1720D. Shroud 1900 may extend from a low-profile annular ring 1900A (FIG. 19) to an extended cylinder 1900C (FIG. 21) so as to cover sharp tip 1712 of needle 1706 when pulled back into a retracted position. As needle 1706 is being removed from a patient, for example, shroud 1900 will from a more elongated cylinder 1900B (FIG. 20) between hinged portions 1720A-1720D until shroud 1900 is deployed to cover sharp tip 1712 as extended cylinder 1900C. In other words, the operation of the movement of the operator pulling handle 1730 upwardly opens the bellows of shroud 1900 as frame 1716 opens to a greater height. This can be used instead of, or in addition to, other protection devices.

A needle trap 2200 may be provided at the end of shroud 1900 or other needle protection devices. Needle trap 2200 has a rounded tip 2202 that has a diameter slightly larger than the diameter of needle 1706. Flaps 2204 are positioned to abut needle 1706 prior to entrapment within shroud 1900 or another needle protection device. Flaps 2204 are resilient and biased to move toward one another, for example, to a flat position when needle 1706 is removed. Flaps 2204 may be positioned relative to one another such that one overlaps the other preventing needle 1706 from going back through needle trap 2200.

The material of flaps 2204 can be a number of semi-rigid plastics, which may include, for example, PVC and polypropylene, or metal. If plastic is used, the both body and flaps 2204 can be manufactured by injection molding techniques in a single process. The thickness and angle of flaps 2240 and may be configured to allow bending closer to the inner wall, so that the needle may be positioned through the end of the needle trap 2200 during assembly time. After needle 1706 is withdrawn into shroud 1900, the inwardly angled flaps 2204 prevents needle 1706 from going through again.

Figure 26:
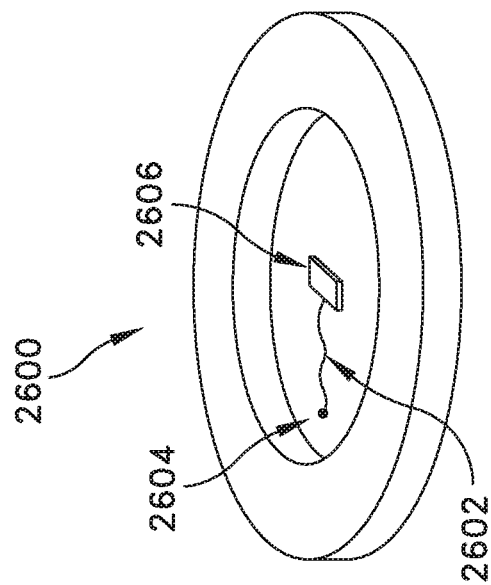
FIGS. 26 and 27 illustrate a flat spring trap with a low-profile configuration and designed to retain needle subsequent to use.
Figure 27:
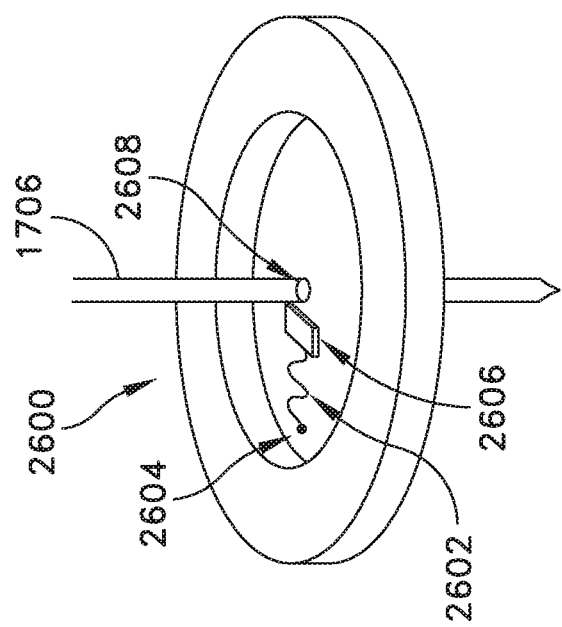

In another embodiment, and referring to FIGS. 26-29, a flat spring trap 2600 has a low-profile configuration with a loaded position and an activated position to retain needle 1706 subsequent to use. Flat spring trap 2600 may be used in place of needle trap 2200 with shroud 1900, or trap 2600 may be used with other needle protection devices. For example, a tempered flat wire forming a flat spring 2602 may be bonded at a point 2604 to a surface of trap 2600. Away from bonded point 2604, a cover 2606 may be in connection with spring 2602. Cover 2606 may have a height substantially equal to spring 2602. Alternatively, cover 2606 may have a different height than spring 2602. An orifice 2608 is positioned through trap 2600 with a size to accommodate needle 1706. During assembly of a needle protection device, spring 2602 and cover 2608 are shifted away from orifice 2608 so that needle 1706 is threaded through orifice 2608. When needle 1706 is withdrawn through orifice 2608, spring 2602 moves cover 2606 to a position near orifice 2608 so as to prevent needle 1706 from again going through orifice 2608. FIG. 26 illustrates needle 1706 configured through trap 2600 in a loaded, ready to use position. FIG. 27 illustrates cover 2606 in an activated position with needle 1706 withdrawn from trap 2600. Trap 2600 is advantageous with a low-profile, an almost flat configuration. For example, spring 2602 may have a thickness of ⅟32 of an inch. In an embodiment, spring 2602 may be made out of stainless steel. In another embodiment, spring 2602 may be stamped or otherwise configured from a plastic material. In an embodiment, spring 2602 may be completely flat to have a total height in the same amount as the thickness of the wire or other material forming the spring.

Figure 29:
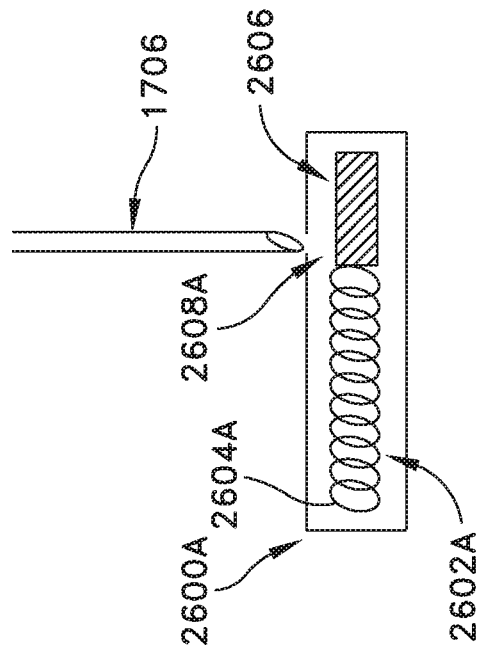
FIGS. 28 and 29 illustrate a trap having a very small diameter spring, which is similar to the flat spring trap shown in FIGS. 26 and 27.
Figure 28:
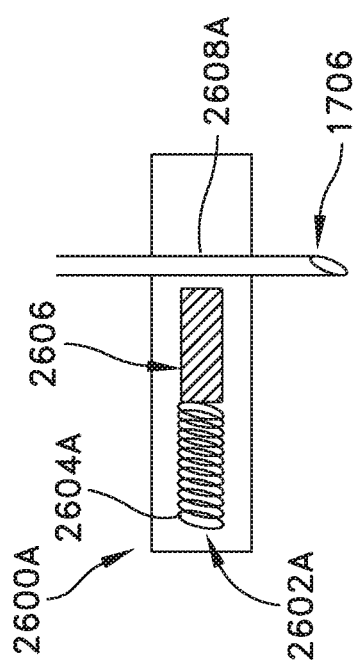

In another embodiment, a trap 2600A includes a very small diameter spring 2602A rather than a flat spring Small diameter spring 2602A may be about ⅟16 of an inch in diameter. Small diameter spring trap 2602A may be used in place of needle trap 2200, or flat spring trap 2600, with shroud 1900, or with other needle protection devices. For example, a spring 2602 may be bonded at a point 2604A to a portion of trap 2600A. Away from bonded point 2604A, a cover 2606A may be in connection with spring 2602A. An orifice 2608A is positioned through trap 2600 with a size to accommodate needle 1706. During assembly of a needle protection device, spring 2602A and cover 2608A are shifted away from orifice 2608A so that needle 1706 is threaded through orifice 2608A. When needle 1706 is withdrawn through orifice 2608A, spring 2602A moves cover 2606A to a position near orifice 2608A so as to prevent needle 1706 from again going through orifice 2608A. FIG. 28 illustrates needle 1706 configured through trap 2600A in a loaded, ready to use position. FIG. 29 illustrates cover 2606A in an activated position with needle 1706 withdrawn from trap 2600A. Trap 2600A is advantageous with a low-profile, an almost flat configuration. In an embodiment, spring 2602A may be a cylindrical minute spring at least as small as 1/16" in diameter or smaller such that the diameter of the spring wire is approximately 20-30 thousandths of an inch.

Figure 30:
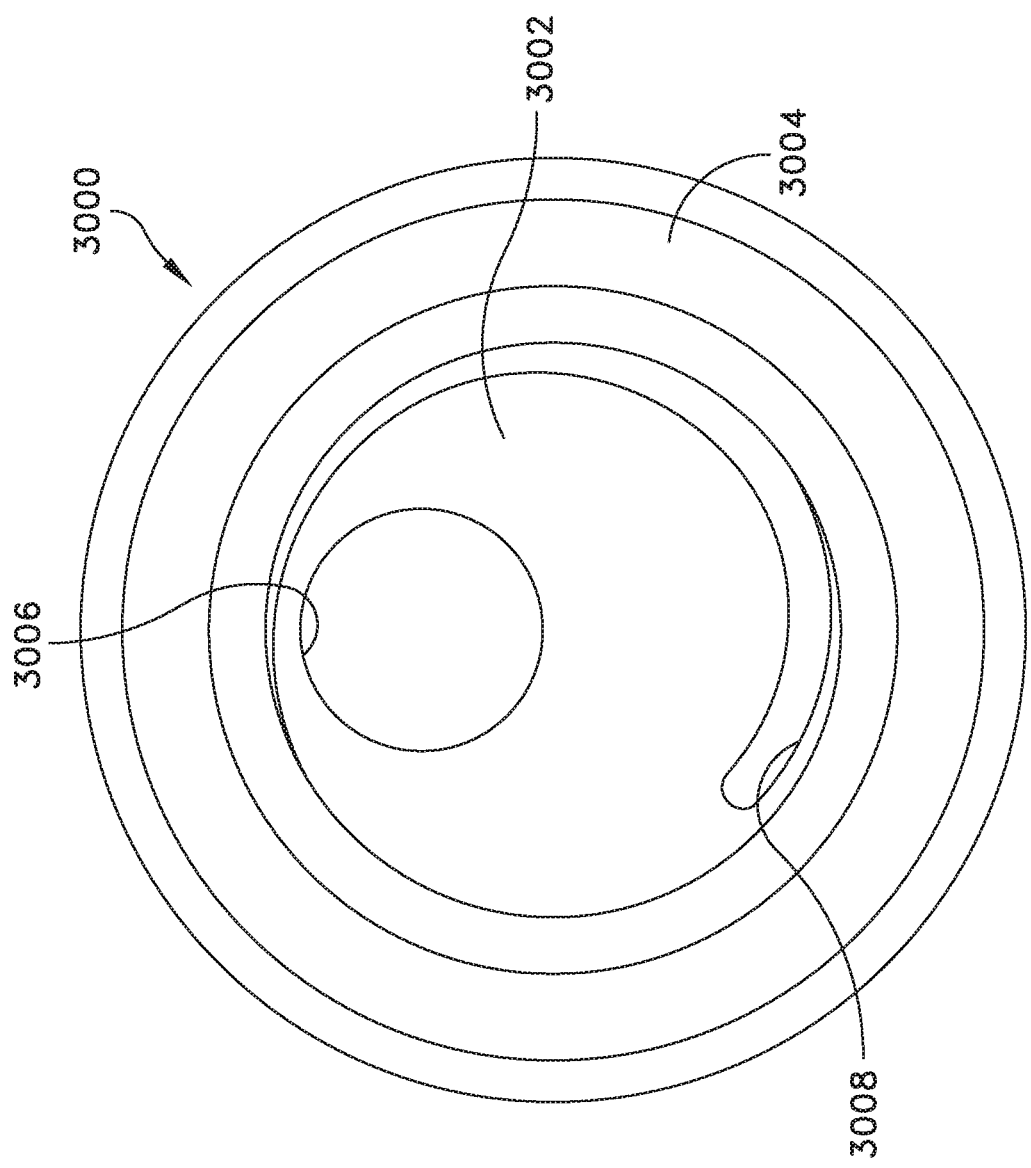
FIGS. 30-32 illustrate a sliding door trap that includes a door portion and a housing portion.
Figure 31:
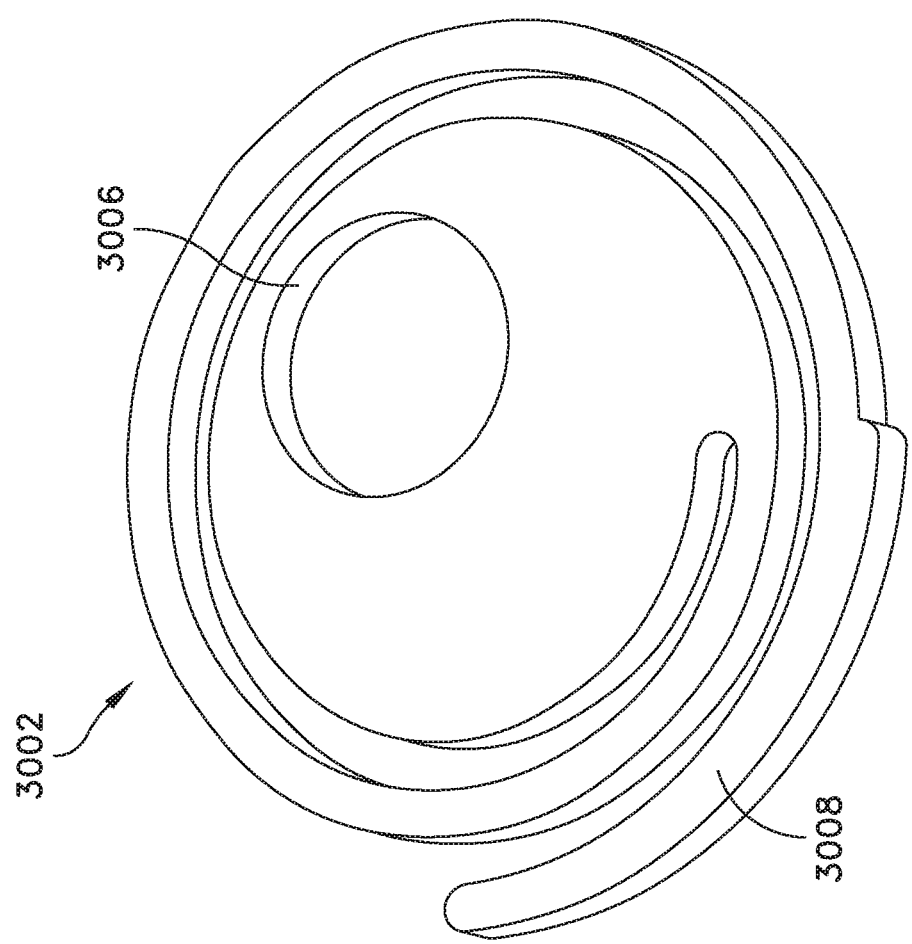
Figure 32:
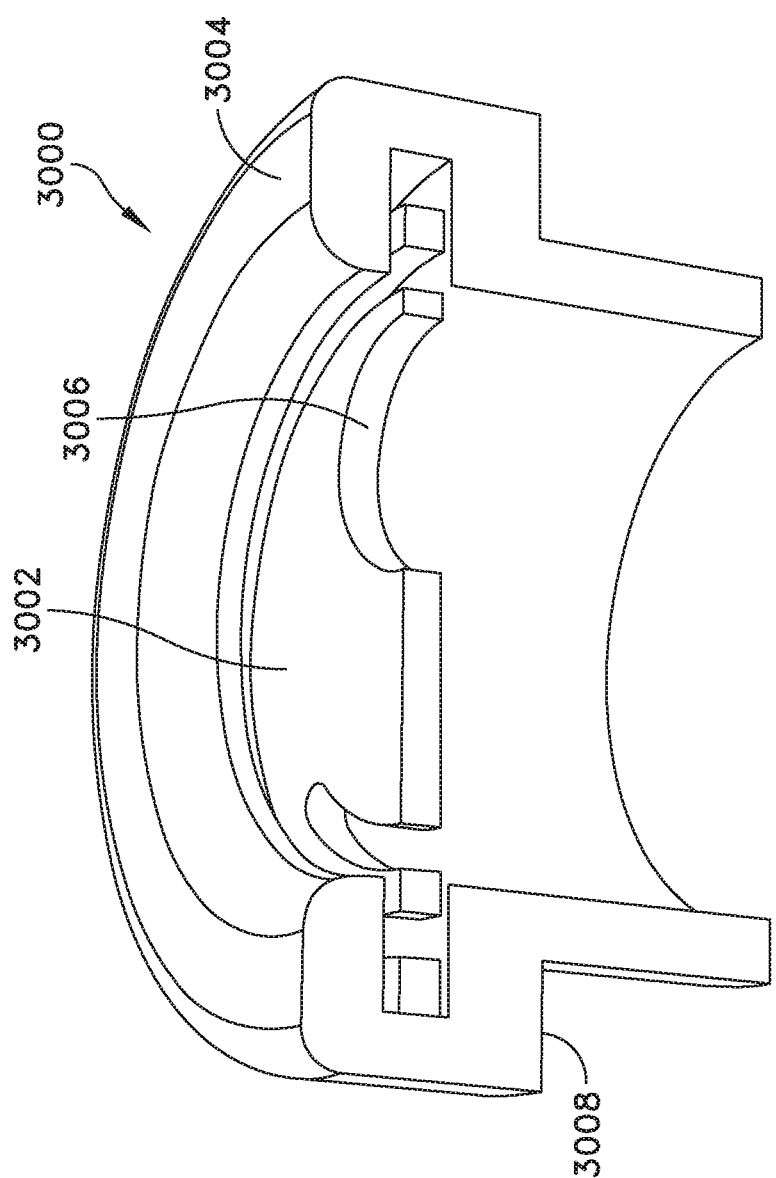

In another embodiment, a sliding door trap 3000 includes a door portion 3002 and a housing portion 3004. An exemplary illustration of sliding door trap 3000 is shown in FIG. 30. One embodiment of door portion 3002 is illustrated in FIG. 31. A cross-sectional view of sliding door trap 3000 is shown in FIG. 30. An opening through door portion 3002 provides an orifice 3006 for a needle. A spring portion 3008 (of door portion 3002 biases against housing portion 3004 so as to move orifice 3006 away from the path of the needle when the needle is removed from orifice 3006. Door portion 3002 may include plastic material, metal, or other types of material. In an embodiment, door portion 3002 has concentric grooves to form biasing spring 3008 and an off-centered orifice 3006. During assembly, orifice 3006 is forced into a concentric position by reducing the space between the spiral grooves of spring 3008 to a minimum. When the needle is withdrawn, door portion 3002 realigns back into a pre-configured natural off-centered position and, thus, the needle cannot go back through to inadvertently stick a user.

Figure 33:
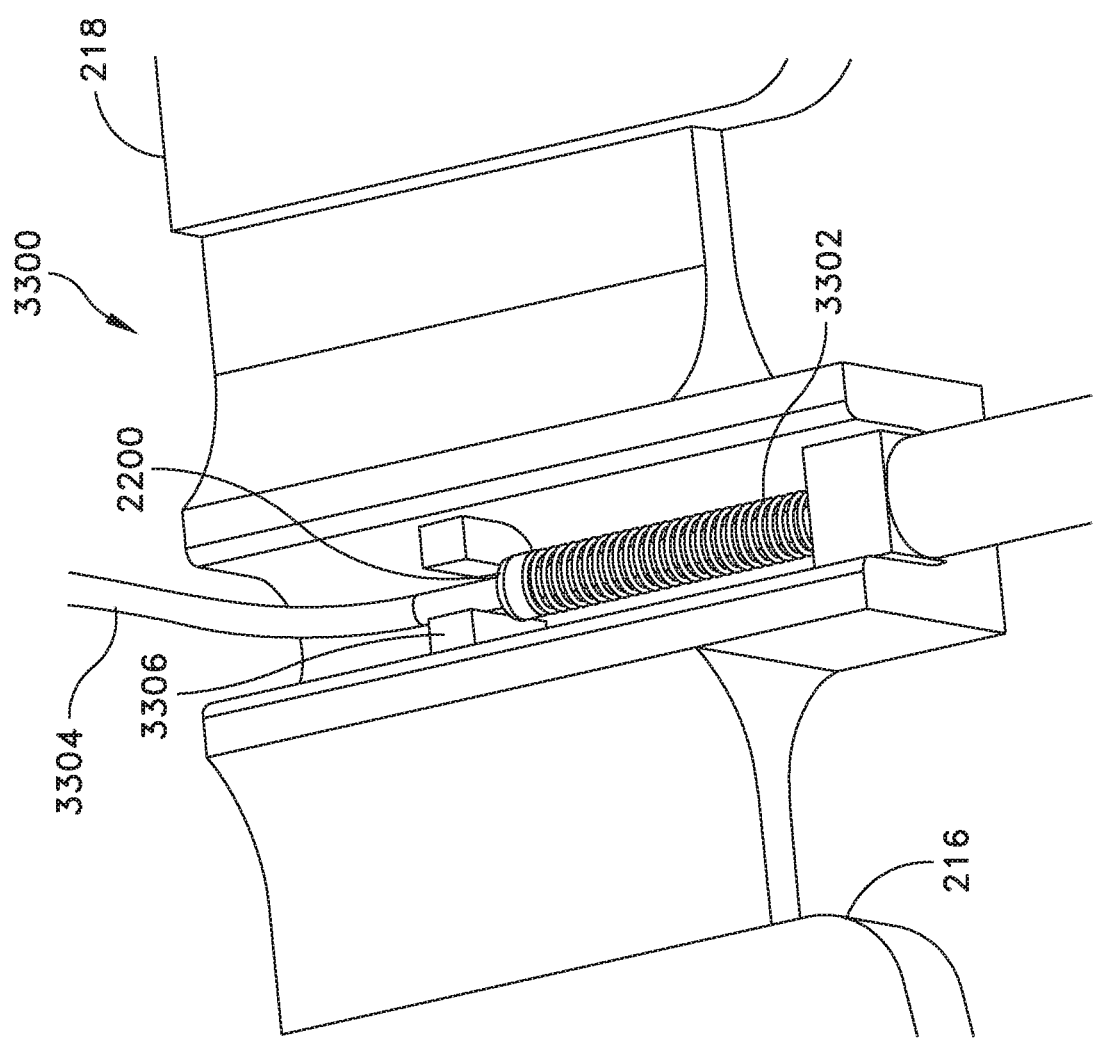
FIGS. 33-36 illustrate a needle protection device that includes a needle covering spring releasably housed in a recess within a central body portion.
Figure 34:
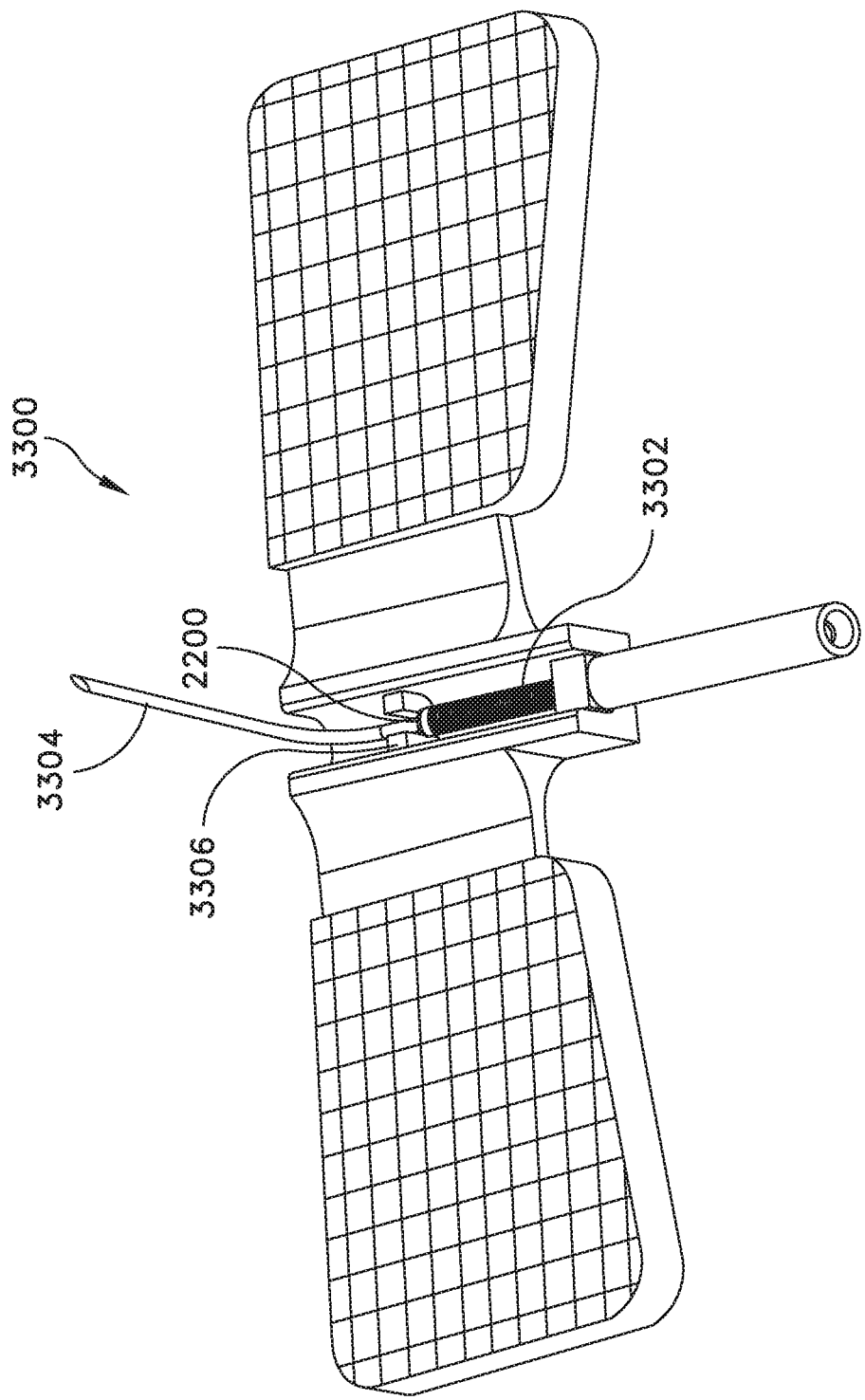
Figure 35:
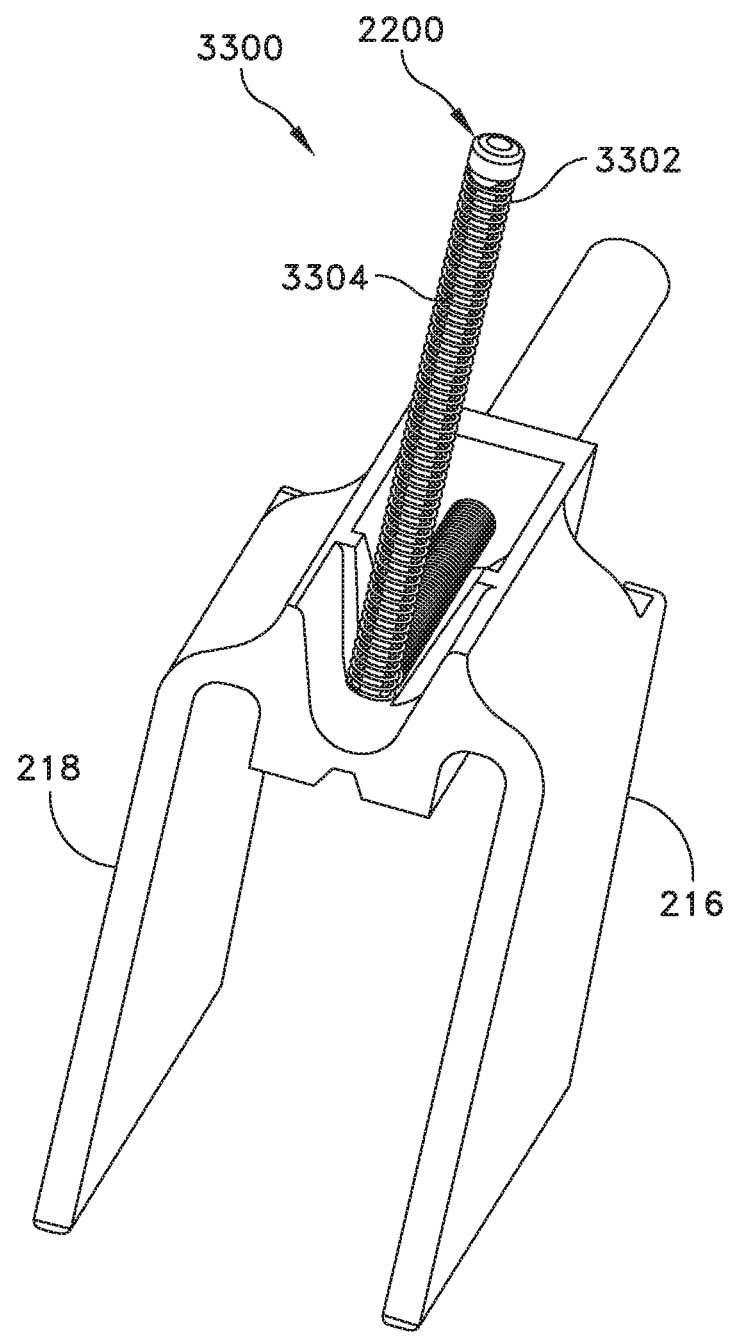
Figure 36:
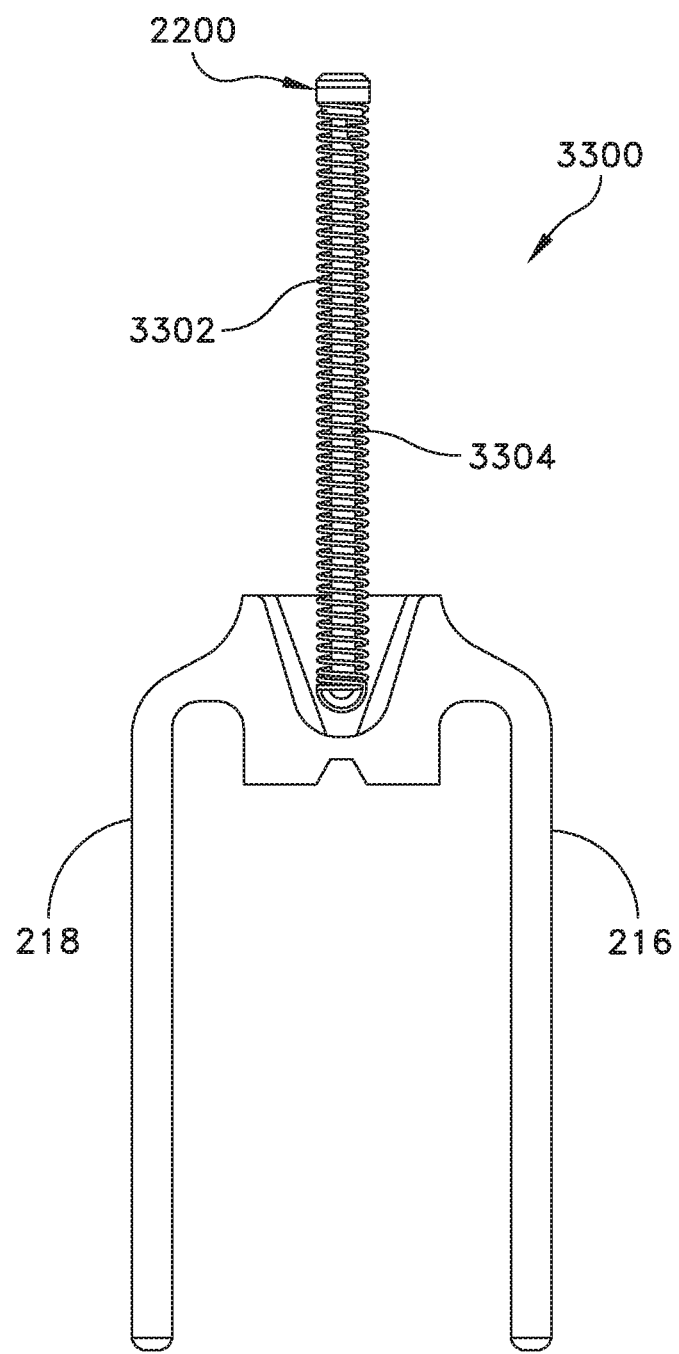

In another embodiment, a needle protection device 3300 includes a needle covering spring 3302 housed in a recess 3303 within central body portion 202. A needle 3304 extends from within needle covering spring 3302 and remains uncovered when needle covering spring 3302 remains within recess 3303. In one embodiment, needle trap 2200 (described hereinabove) or another end portion of spring 3302 may engage an abutment 3506. To release spring 3302 after a procedure is completed, abutment 3306 may be actuated to allow needle trap 2200 and a portion of spring 3304 to travel toward the end of the needle. Needle trap 2200 may operate as described above or the spring may operate in another matter, such as simply covering the end of the needle. One way to release spring 3304 is to move portions 3306A and 3306B of abutment 3306 in connection with wings 216, 218 apart from one another. FIGS. 33 and 34 illustrate one embodiment of device 3300 with abutment 3306 prior to actuation in a loaded configuration. FIGS. 35 and 36 correspond with illustrate device 3300 after actuation with spring 3302 actuated to cover needle 3304.

Regarding the polygonal design FIG. 17, one variation of such is a multi-axis polygon which is covered all around. Imagine two triangular pyramids with their bases attached such that the needle is not visible from any side and thus there is no possibility for any finger to be placed close to the needle at any time during the withdrawal.

Regarding the patient adhesive on the bottom of the polygonal design, such adhesive provides an added level of safety because the clinician places one hand over this layer with the adhesive still on the patient while the needle is being withdrawn from the patient and thus the needle reaches the inside of the "accordion" while the clinicians hands are busy (one with the lower layer and the other with pulling up the top layer—and thus further reducing the possibility of the needle reaching the clinician).

Most safety devices require complex mechanisms to trap the needle. The devices of the present invention provide simpler, easier to manufacture, and yet modifiable, products that satisfy additional clinical requirements beyond safety. These additional requirements include lower profile, flexibility, customizability, patient comfort, and scalability.

Lower profile is critical for patients that wear these devices during prolonged periods of time. Flexibility of the devices is unique as most other safety devices are made from stiff, mechanically complex plastics. The geometry of these designs can be modified to satisfy specific criteria, including the need to use this device with a "dual implanted port," which may be limited by a larger footprint of other existing devices, and various clinical preferences. Patient comfort is provided in that softer materials are in contact with patient. The ability to use materials that minimize patient allergenic reactions. As discussed above, lower profile and smaller footprint reduce patient discomfort. Scalability is achieved in that various design features may be used in conjunction with one another as desired.

The present disclosure is provided to allow practice of the invention, after the expiration of any patent granted hereon, by those skilled in the art without undue experimentation, and includes the best mode presently contemplated and the presently preferred embodiment. Nothing in this disclosure is to be taken to limit the scope of the invention, which is susceptible to numerous alterations, equivalents and substitutions without departing from the scope and spirit of the invention.

The invention claimed is:

1. A device for protecting a user from a sharp tip of a medical needle, the device comprising:
 a central body in fluid connection with a delivery tube;
 a medical needle including:
  a first end in fluid connection with the delivery tube; and
  a second end distal from the central body, the second end including the sharp tip;
 a pair of wings each extending from, and attached at one end to, opposing sides of the central body and positioned with the medical needle therebetween, the pair of wings being selectively positionable from an open position, in which the wings leave the needle exposed so as to permit the medical needle to be placed into a patient, to a closed position in which the pair of wings are folded over the needle, wherein each wing of the pair of wings includes an inner surface; and
 a hook-and-loop fastening system disposed in a circular recess on the inner surface of each wing of the pair of wings, the hook-and-loop fastening system configured to selectively attach each inner surface of the pair of wings together to one another in the closed position with the medical needle positioned therebetween.

2. The device of claim 1, wherein the hook-and-loop fastening system includes a hook material disposed on the inner surface of one of the pair of wings and a loop material disposed on the inner surface of the other wing of the pair of wings.

3. The device of claim 1, wherein the hook-and-loop fastening system includes a hook material on a first of the wings with a profile lower than an outer surface of the first of the wings and a loop material on a second of the wings with a profile lower than an outer surface of the second of the wings.

4. The device of claim 1, wherein the hook-and-loop fastening system includes a hook material on each wing of the pair of wings and a loop material on each wing of the pair of wings.

5. The device of claim 1, wherein the hook-and-loop fastening system includes a hook material on one wing of the pair of wings and a loop material on the other wing of the pair of wings, and an adhesive material within at least one of the hook material and the loop material.

6. The device of claim 5, wherein the adhesive material includes at least one of a) a glue primer and a glue, b) an instant glue, and c) a gel carrier incorporating the adhesive material.

7. The device of claim 1, further including a second mechanical fastener not including a hook-and-loop fastening system.

8. The device of claim 1, further including a lip extending along at least a portion of the perimeter of at least one of the wings of the pair of wings, and a mating portion formed along at least a portion of the perimeter of the other wing of the pair of wings.

9. The device of claim 1, wherein at least one wing of the pair of wings is formed from at least one of a rigid material, a semi-rigid material, a soft material, a gel material, a cloth material, and a non-woven cloth material.

10. The device of claim 1, wherein at least one wing of the pair of wings is one of a circular shape and a rectangular shape.

11. A method of protecting a user from a sharp tip of a medical needle, the method comprising:
obtaining a device according to claim 1;
inserting the sharp tip of the medical needle into a patient;
withdrawing the sharp tip of the medical needle from the patient;
closing the pair of wings with the medical needle positioned therebetween; and
fastening the inner surface of each of the pair of wings together with the hook-and-loop fastening system.

12. A device for protecting a user from a sharp tip of a medical needle, the device comprising:
a central body in fluid connection with a delivery tube;
a medical needle including:
a first end in fluid connection with the delivery tube;
a second end distal from the central body, the second end including the sharp tip;
a pair of wings symmetrically extending from the central body, the pair of wings being selectively positionable from an open position along a common plane with the medical needle position therebetween, in which the wings leave the needle exposed so as to permit the medical needle to be placed into a patient, to a closed position in which the pair of wings are folded over the needle, wherein each wing of the pair of wings includes a circular recess on an inner surface, each circular recess having a fastening element positioned therein.

13. The device of claim 12 further comprising: a hook-and-loop fastening system disposed on the inner surface of each wing of the pair of wings and comprising the fastening element, the hook-and-loop fastening system configured to selectively attach each inner surface of the pair of wings together to one another in the closed position with the medical needle positioned therebetween.

14. The device of claim 13, wherein the hook-and-loop fastening system includes a hook material disposed on the inner surface of one of the pair of wings and a loop material disposed on the inner surface of the other wing of the pair of wings.

15. The device of claim 13, wherein the hook-and-loop fastening system includes a hook material on each wing of the pair of wings and a loop material on each wing of the pair of wings.

16. The device of claim 13, wherein the hook-and-loop fastening system includes a hook material on one wing of the pair of wings and a loop material on the other wing of the pair of wings, and an adhesive material within at least one of the hook material and the loop material.

17. The device of claim 16, wherein the adhesive material comprises a gel carrier incorporating the adhesive material.

18. The device of claim 13, further including a second mechanical fastener not including a hook-and-loop fastening system.

19. The device of claim 12, further including a lip extending along at least a portion of the perimeter of at least one of the wings of the pair of wings, and a mating portion formed along at least a portion of the perimeter of the other wing of the pair of wings.

20. An apparatus comprising:
a central body in fluid connection with a delivery tube;
a medical needle including:
a first end in fluid connection with the delivery tube; and
a second end distal from the central body, the second end including the sharp tip;
a pair of wings each extending from, and attached at one end to, opposing sides of the central body and positioned with the medical needle therebetween, the pair of wings being selectively positionable from an open position, in which the wings leave the needle exposed so as to permit the medical needle to be placed into a patient, to a closed position in which the pair of wings are folded over the needle, wherein each wing of the pair of wings includes an inner surface; and
securing means comprising a carrier gel to selectively attach each inner surface of the pair of wings together in the closed position with the medical needle positioned therebetween.

* * * * *